(12) United States Patent
O'Day et al.

(10) Patent No.: US 11,366,102 B2
(45) Date of Patent: Jun. 21, 2022

(54) SPECTOGRAPHIC METABOLITE-SIGNATURE FOR IDENTIFYING A SUBJECT'S SUSCEPTIBILITY TO DRUGS

(71) Applicant: Olaris, Inc., Cambridge, MA (US)

(72) Inventors: Elizabeth M. O'Day, Watertown, MA (US); Chen Dong, Boston, MA (US); Bo Zhang, Monmouth Junction, NJ (US); Srihari Raghavendra Rao, Waltham, MA (US)

(73) Assignee: Olaris, Inc., Camrbidge, MA (US)

( * ) Notice: Subject to any disclaimer, the term of this patent is extended or adjusted under 35 U.S.C. 154(b) by 462 days.

(21) Appl. No.: 16/597,402

(22) Filed: Oct. 9, 2019

(65) Prior Publication Data
US 2020/0116703 A1     Apr. 16, 2020

Related U.S. Application Data

(60) Provisional application No. 62/745,849, filed on Oct. 15, 2018.

(51) Int. Cl.
*G01N 33/50* (2006.01)
*G01N 24/08* (2006.01)
*A61B 5/055* (2006.01)
*G01R 33/465* (2006.01)

(52) U.S. Cl.
CPC ....... *G01N 33/5038* (2013.01); *G01N 24/082* (2013.01); *G01N 24/088* (2013.01); *G01N 2800/52* (2013.01)

(58) Field of Classification Search
CPC ............... G01N 24/08; G01N 33/5038; G01N 2800/52; A61B 5/055; G01R 33/465
See application file for complete search history.

(56) References Cited

U.S. PATENT DOCUMENTS

| | | | |
|---|---|---|---|
| 2003/0138377 A1* | 7/2003 | Leyland-Jones | C12Q 1/48 424/9.2 |
| 2005/0074745 A1* | 4/2005 | Clayton | G01N 33/5038 702/19 |
| 2006/0028301 A1 | 12/2006 | Boros | |
| 2008/0220530 A1 | 11/2008 | Bahn et al. | |
| 2010/0273661 A1* | 10/2010 | Qiu | G01N 33/6893 436/71 |
| 2013/0065255 A1 | 3/2013 | Flores et al. | |
| 2015/0005243 A1 | 1/2015 | O'Day et al. | |
| 2018/0045727 A1* | 2/2018 | Spetzler | G01N 33/57415 |

OTHER PUBLICATIONS

Zhang et al., NMR-Based Metabolomics and Its Application in Drug Metabolism and Cancer Research. Curr Pharamcol Rep (2016) 2:231-240.

* cited by examiner

*Primary Examiner* — Christopher Adam Hixson
(74) *Attorney, Agent, or Firm* — Karl Bozicevic; Bozicevic, Fields & Francis LLP

(57) ABSTRACT

A method of predicting the responsiveness of a patient to a pharmaceutical drug by measuring metabolites in a biological sample from the patient is disclosed. Specific drug metabolites in blood from breast cancer patients are analyzed using NMR spectroscopy whereby responsiveness of the human cancer patients before, during and after treatment with a cancer drug is assessed by measuring the change in clinical outcomes. Data obtained is used to identify particular NMR resonances that are strongly correlated with whether the patient is responsive or resistant to each drug. As such, models for predicting the responsiveness of a patient to each drug based on metabolites from the patient are provided.

19 Claims, 18 Drawing Sheets

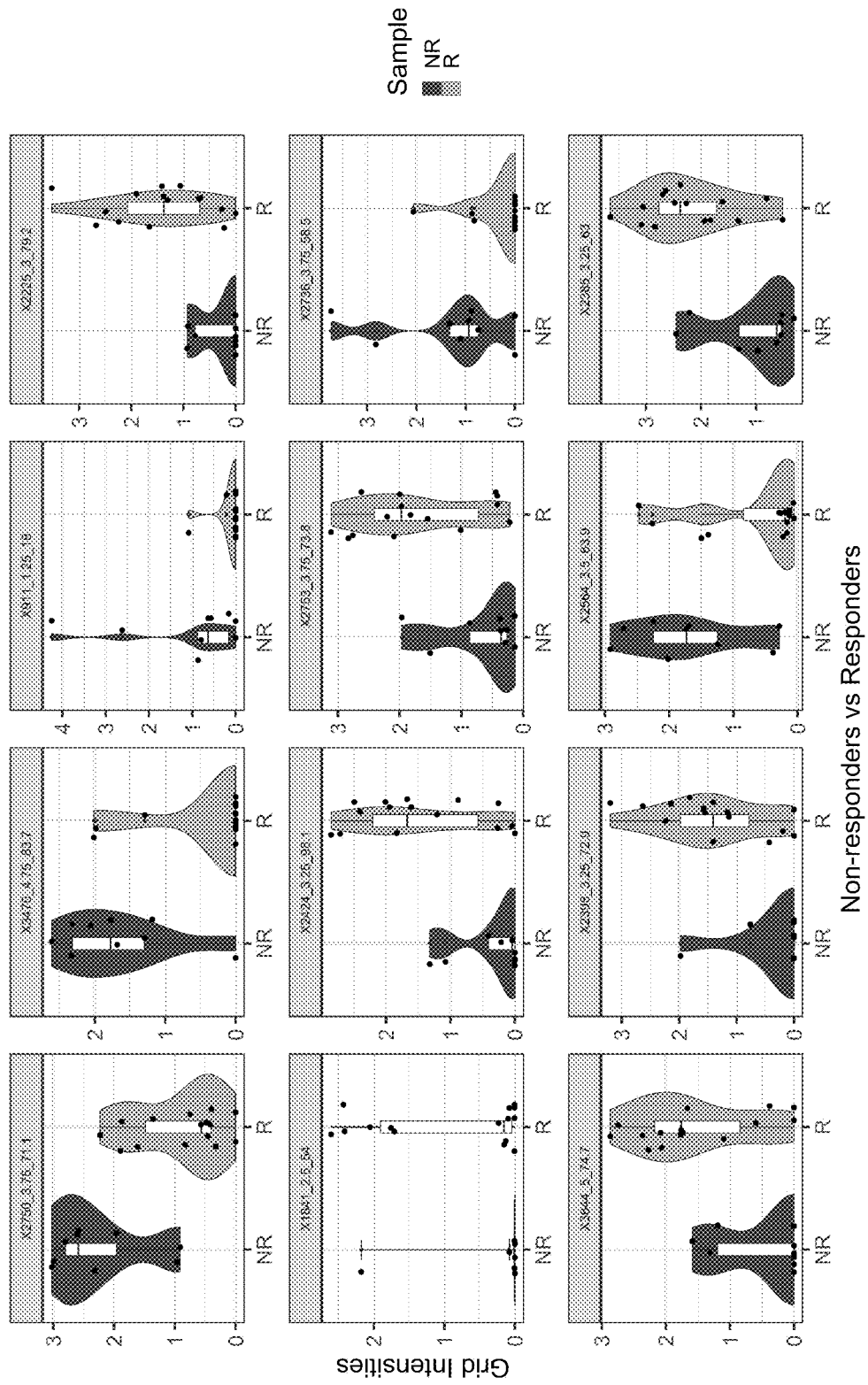

Figure 3

| Metabolite or Resonance (1H +/- 0.25x13C +/- 0.9) | INCREASED or DECREASED in NR |
|---|---|
| Fructose | INCREASED |
| Galactose | INCREASED |
| Lactic acid | INCREASED |
| Acetylcholine | INCREASED |
| Glutamic acid | DECREASED |
| Adipic Acid | INCREASED |
| Arginine | DECREASED |
| alpha ketoglutarate | INCREASED |
| alanine | DECREASED |
| acetylornithine | DECREASED |
| 3.75x71.1 | INCREASED |
| 4.8x84.4 | INCREASED |
| 3.2x79.8 | DECREASED |
| 2x24.3 | DECREASED |
| 2.5x54 | DECREASED |
| 1.25x18 | INCREASED |
| 3.0x79.2 | DECREASED |
| 3.75x58.5 | INCREASED |
| 4.75x83.7 | INCREASED |
| 5x74.7 | DECREASED |

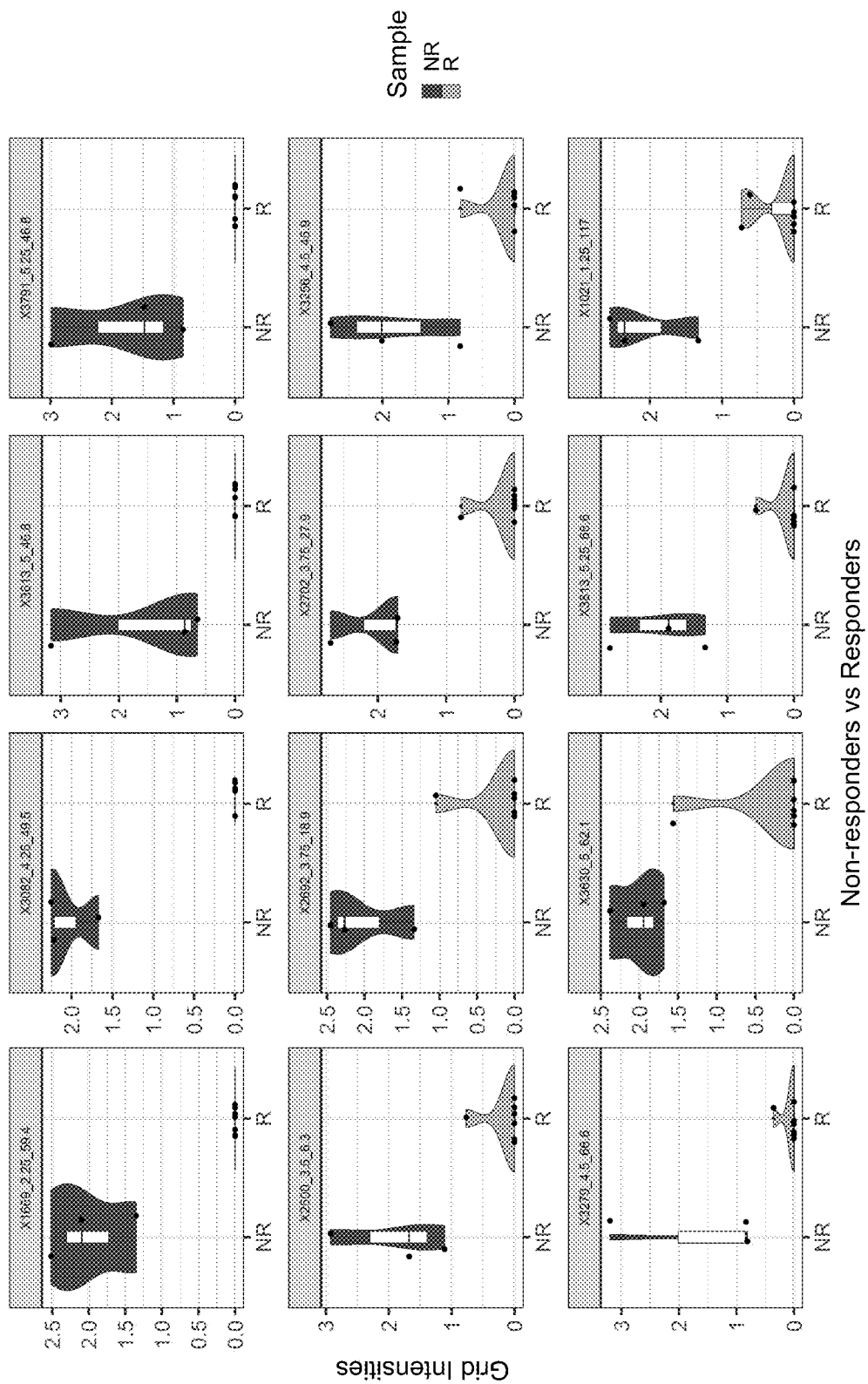

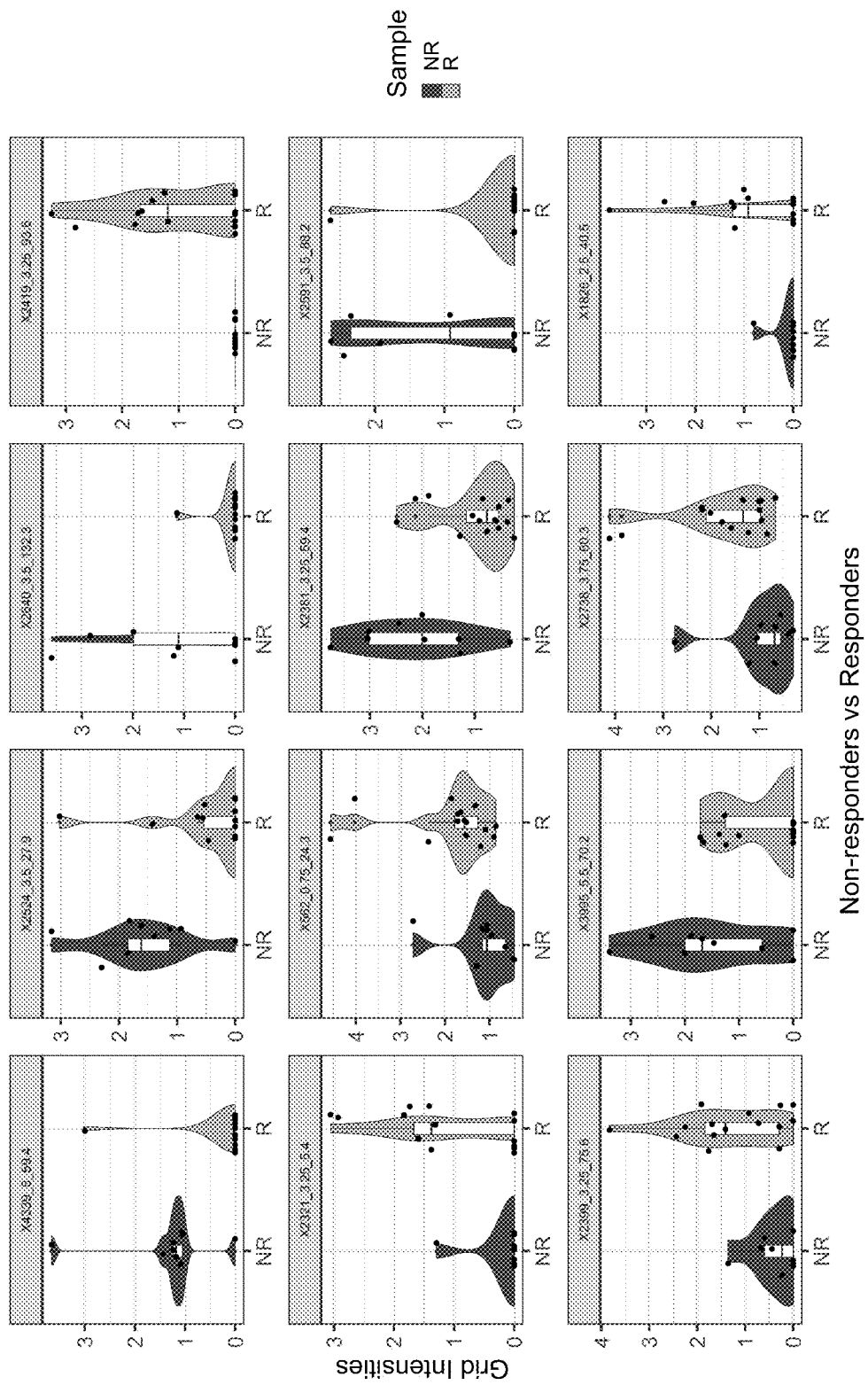

Figure 6

| Metabolite or Resonance (1H +/- 0.25x13C +/- 0.9) | INCREASED or DECREASED in NR |
|---|---|
| 3.5x27.9 | INCREASED |
| D-Glucuronic acid | DECREASED |
| Glucose 6-phosphate | DECREASED |
| Glycocholic acid | DECREASED |
| L-Leucine | DECREASED |
| Oxalacetic acid | INCREASED |
| L-Tyrosine | INCREASED |
| 6x59.4 | INCREASED |
| Mannobiose | DECREASED |
| 2.25x28.8 | INCREASED |
| 3.25x59.4 | INCREASED |
| 3.25x75.6 | DECREASED |
| 3.5x78.3 | DECREASED |
| 3.75x79.2 | DECREASED |
| 0.75x24.3 | DECREASED |

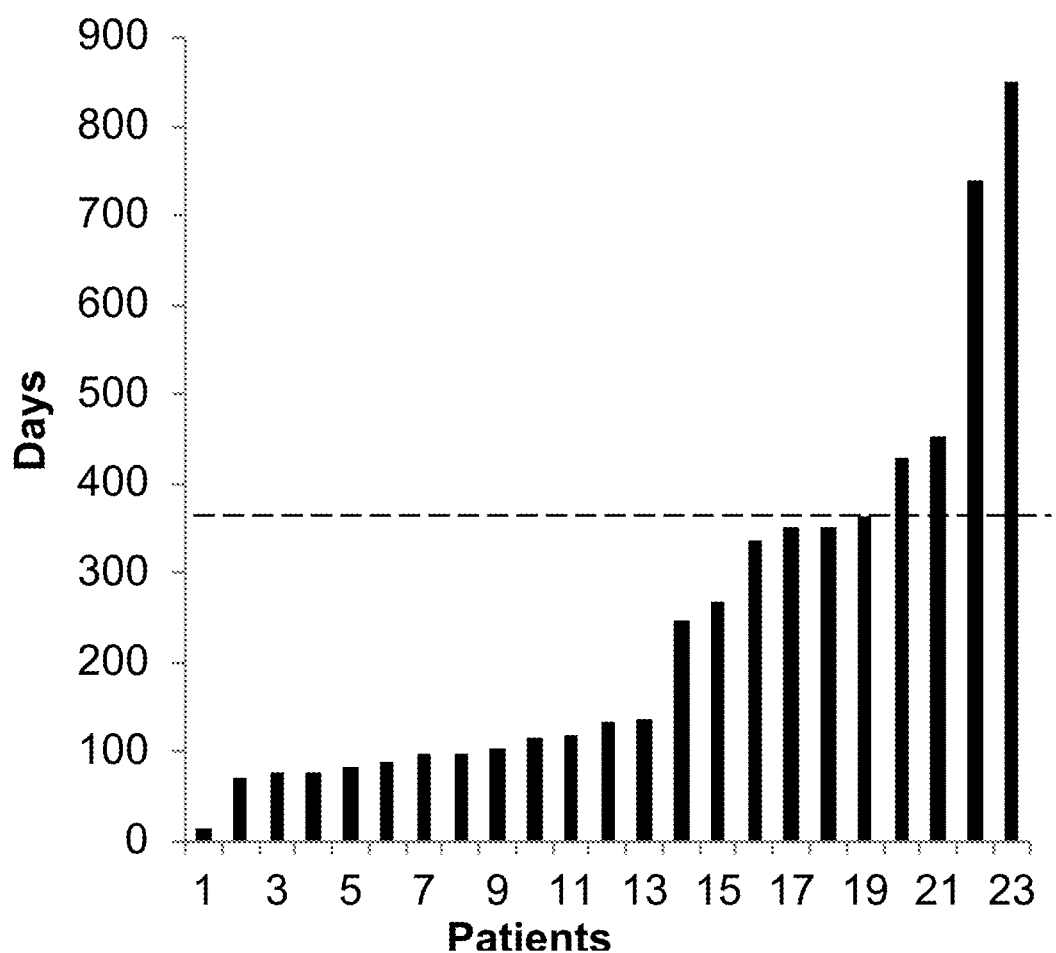

Figure 9

| Metabolite or Resonance (1H +/- 0.25x13C +/- 0.9) | INCREASED or DECREASED in NR |
|---|---|
| Glucose | DECREASED |
| NADPH | DECREASED |
| Lauric Acid | INCREASED |
| Pentadecanoic acid | INCREASED |
| Heptadecanoic acid | INCREASED |
| 3x73.8 | DECREASED |
| 3x97.2 | INCREASED |
| Isovaleric acid | DECREASED |
| Serine | DECREASED |
| 3.25x72 | DECREASED |
| 3.5x53.1 | DECREASED |
| 3.75x585.5 | DECREASED |
| 1x32.4 | DECREASED |

Figure 11

| Metabolite or Resonance (1H +/- 0.25x13C +/- 0.9) | INCREASED or DECREASED in NR |
|---|---|
| Indole-3-lactic acid | INCREASED |
| isoleucine | INCREASED |
| homoserine | INCREASED |
| 3.75x77.4 | INCREASED |
| 0.75x23.4 | DECREASED |
| 3.25x69.3 | INCREASED |
| 3.25x90.9 | DECREASED |
| 3.75x61.2 | INCREASED |
| 4.5x74.7 | INCREASED |

SPECTOGRAPHIC METABOLITE-SIGNATURE FOR IDENTIFYING A SUBJECT'S SUSCEPTIBILITY TO DRUGS

The invention relates generally to analysis of metabolites in a patient biofluid such as blood, urine, feces, cerebral fluid, saliva or in an extraction from tissue including tumor tissue. The sample from a patient can be analyzed or scanned with spectroscopy to determine the profile of certain metabolites and the profile used in order to determine the likelihood a patient will be responsive or resistant to a particular drug or therapy.

FIELD OF THE INVENTION

This present invention relates to biomarkers associated with therapeutic response. These biomarkers include endogenous metabolites, microbiome byproducts and xenobiotics and are useful for predicting the likelihood a patient will be responsive or resistance to a particular drug or therapy.

BACKGROUND OF THE INVENTION

Precision medicine (PM) utilizes molecular-level information and environmental data from an individual to guide medical decisions. Biological markers, so called "biomarkers" are the cornerstone of PM. Biomarkers have been identified to stratify individuals into subpopulations that differ in their susceptibility to a particular disease, prognosis of disease, and response to specific treatment.

Clinicians use biomarkers that include altered expression of DNA, RNA, proteins, metabolites or combinations thereof to direct a clinical action. Using breast cancer as an example, it is routine for oncologists to isolate tumor tissue through a biopsy and perform both genomic sequencing and protein immunohistochemistry. The expression profile of specific biomarkers in the tumor tissue will determine specific treatment options. If a patient has increased expression of the estrogen receptor or progesterone receptor, so called "hormone receptor-positive" (HR+) they would likely receive endocrine therapy (ET) such as tamoxifen or an aromatase inhibitor, which aims to block estrogen signaling. However, if a patient displays amplification of human epidermal growth factor receptor 2 (HER2+) they are directed towards an anti-HER2 therapy such as trastuzumab. There are additional biomarker tests, such as the OncotypeDX 21-gene panel assay, which are used to determine aggressiveness of the malignancies and whether chemotherapy should supplement ET. Similar biomarkers exist to guide targeted therapies for other cancers such as use of the tyrosine kinase inhibitor, imatinib, upon detection of the BCR-ABL fusion gene in chronic myeloid leukemia or overexpression of c-kit in gastrointestinal stromal tumors. Vemurafenib and dabrafenib are therapies recommended for melanoma patients with specific V600E mutations in the BRAF gene.

Unequivocally these biomarkers and their respective targeted therapies have dramatically improved patient outcomes. However, the biomarkers and therapies are far from perfect. Variable drug response rates lead to mixed patient outcomes. For example, despite increased expression of c-kit, imatinib has no effect on adenoid cystic carcinomas of the salivary gland. Colorectal cancers harboring the same BRAF V600E mutations display response rates less than 10% compared to 57% in melanoma. Further, after 9-12 months of treatment approximately half of V600E BRAF-mutated melanoma patients will stop responding to treatment and see their tumors relapse. Relapse rates are even higher for HER2+ metastatic breast cancer patients treated with trastuzumab, where after about 1 year of progression free survival (PFS) approximately 75% of patients will stop responding to therapy. Further, approximately 30%-50% of ER+ breast cancer patients will recur after ET. ET-resistant tumors also tend to stay dormant for many years, in some cases metastasis can be triggered as late as 20 years after initial diagnosis. Mortality from these ET-resistant tumors accounts for the majority of breast cancer deaths in the United States each year.

Drug resistance (intrinsic and acquired) contribute to the variable patient outcomes. Patients are considered to have intrinsic resistance to therapy when no clinical benefit is observed following initial treatment. Acquired resistance differs in that disease progression occurs after an initial period of response. The differences between intrinsic and acquired resistance are not clear, and it is possible that each operates through different mechanisms.

Patient heterogeneity, tumor microenvironment, crosstalk between signaling pathways, complex biological pathways, the microbiome, environmental factors and more, contribute to resistance. Being able to detect intrinsic and/or acquired resistance to alter a patient's therapy remains a long-standing goal of PM.

"Biomarkers of response" (BoR) are a subset of biomarkers that are capable of identifying patients that will respond (Responders—"R") and those that will not respond (Non-Responders—"NW") to specific therapies. Baseline BoRs offer predictive factors to optimize initial treatment by identifying intrinsically resistant patients. On-treatment BoRs detect acquired resistance, enabling cycling therapies that have become ineffective for those more likely to benefit a patient. BoRs also have the potential to diminish unnecessary exposure to side effects and reduce unnecessary costs.

Several large-scale genomic efforts to uncover BoRs have had limited success. Early sequencing efforts relied on genotyping, or detecting a specific genomic mutation. However, because there are millions of genetic mutations that could contribute to a drug working or not working in individual these efforts overlooked important markers. To compensate larger sequencing efforts and in some cases whole-genome sequencing have commenced. However, because we do not understand the complicated and intricated pathways of how mutations interact with other mutations this also failed to deliver consistent success. Thus, there are limited biomarker tools available for clinicals to monitor drug response and resistance for specific therapies.

Recent advancements in metabolomics offer new promise to identify BoRs with bona-fide clinical utility. Metabolites are the small molecules being catabolized and anabolized in an individual to provide energy and biomass. The levels of metabolites are encoded by the genome, but also influenced by inputs from the environment such as diet and the microbiome. Thus, the metabolic output is the closest readout of phenotype, relying what "is actually happening" in a particular patient. By mapping the metabolome it is feasible to construct a metabolic fingerprint for drug response and drug resistance.

Oncology is the area where PM has made the most progress. Yet, nearly all therapeutic areas need BoRs. For example, schizophrenia is a severe neuropsychiatric disorder that affects approximately 0.5-1% of the population. Response to antipsychotic therapy is highly variable and it is not currently possible to predict those patients who will or will not respond to antipsychotic medication. Furthermore, a high percentage of patients, approximately 30% are classified as treatment-resistant schizophrenia (TRS) or intrinsically resistant. Other CNS diseases, neurodegenerative diseases, autoimmune disorders, cardiology, fertility, dermatology, endocrinology, gastroenterology, infectious disease, asthma, pneumonia and many more are additional areas where BoRs are being investigated. Olaris has developed a broad platform using spectrographic metabolite signatures for identifying a subject's susceptibility to drugs. This invention will empower clinicians to incorporate BoRs into treatment decisions to improve patient outcomes.

SUMMARY OF THE INVENTION

A method of treatment is disclosed whereby a drug is administered to a patient wherein the patient has been predetermined as being responsive to a particular drug based on a metabolic profile of components in the patient's sample (blood, urine, feces, cerebral fluid, saliva or tissue extract). Metabolites from the patient sample can be extracted and analyzed. The analysis determines the presence, absence and ratio of metabolites and may be via spectroscopy such as by scanning the patient's sample with NMR spectroscopy, mass spectroscopy or other spectroscopy means, and the resulting scan compared to previous scans or a standard developed based on a statistically significant group of patients taking the drug in order to identify the probability that the patient is resistant to or a responder to a particular drug.

The method of the invention can be utilized with patients who have never taken a particular drug before, or continually used on a patient who is continually dosed with the drug. The analysis can be used in order to determine if a patient is developing resistance to treatment over time and thereby make it possible to discontinue treatment and/or to switch treatment to a different drug after a degree of drug resistance has developed with respect to the initial drug. Thus, the invention is applicable with respect to patients who naturally have a resistance to or ability to respond to a particular drug as well as patients who may have been successfully treated to some degree with a drug and then developed a resistance to treatment with that drug.

Another aspect of the invention is a method of determining whether or not a patient will be responsive to a drug by obtaining a biological sample from the patient which may be blood, plasma, urine, cerebral fluid, saliva or a tissue sample and analyzing metabolites within the biological sample from the patient wherein the analysis may be carried out with spectroscopy such as NMR spectroscopy to create a scan of the sample which is compared within previous scans or a standard in order to develop a statistically significant biomarker of response (BoR) indicating that the patient is resistant to a or a responder to a particular drug.

Another aspect of the invention is a kit which is comprised of the pharmaceutically active drug and a label comprised of instructions indicating administration of the drug is only permitted beyond a given period when the patient has been shown to match a data array based on blood, urine, feces, cerebral fluid, saliva or tissue metabolite components of the patient wherein the data array may be developed by spectroscopy including NMR spectroscopy.

Another aspect of the invention is treating a patient by administering to the patient a drug wherein the patient has been predetermined as a responder to the drug based on a metabolic profile of components of a biological sample from the patient such as the patient's blood, urine, feces, cerebral fluid, saliva or tissue wherein the biological profile is developed by means such as spectroscopy including NMR spectroscopy.

One aspect of the invention makes it possible to screen an individual breast cancer patient for her likelihood of being responsive or resistant to specific CDK4/6 inhibitors, endocrine therapies, tamoxifen, aromatase inhibitors, anti-Her2 therapies, trastuzumab and to personalize treatment for the most optimal outcome.

An aspect of the invention includes analyzing plasma-based metabolites from a baseline (pre-dose) sample and then further analyzing after 2-months of treatment of women with ER+/HER2− metastatic BC treated with CDK4/6 inhibitors, palbociclib and ribociclib. By correlating the metabolite expression profiles to clinical outcomes, it is possible to identify a metabolic signature that differentiates the CDK4/6 Responders ("R") and Non-responders ("NR") patients.

Another aspect of the invention includes identifying separate signatures of response and resistance specific to palbociclib and ribociclib. The method makes it possible to determine 1) the likelihood an individual patient is a CDK4/6 R or NR, 2) which CDK4/6 inhibitor will be most appropriate and 3) to monitor if that therapy is effective or not for that individual patient.

An aspect of the invention includes analyzing serum-based metabolites from a baseline (pre-dose) sample women with HER2+ metastatic BC treated with trastuzumab. By correlating the metabolite expression profiles to clinical outcomes, it is possible to identify a metabolic signature that differentiates the trastuzumab Responders ("R") and Non-responders ("NW") patients.

An aspect of the invention is a method of treating a patient, comprising administering a drug to a patient wherein the patient has been predetermined as a responder to the drug based on a metabolic profile of components of the patient's blood.

An aspect of the invention includes a method of treating a patient, comprising:
administering a drug to a patient wherein the patient has been predetermined as a responder to the drug based on a metabolic profile of components of a sample selected from the group consisting blood, urine, feces, cerebral fluid, saliva and tissue extract, and may further include analyzing blood components of the patient by obtaining a scan of a blood sample of the patient; and
may further include analyzing components of the sample using spectroscopy; obtaining an array of data on the sample from the spectroscopy, and
wherein data obtained is compared to data obtained on samples taken from a statistically significant number of patients administered the same drug and determining a Biomarker of Response in patients based on patient response to the drug and further including counseling the patient regarding medical options based on data;
wherein the scan is obtained using NMR spectroscopy, wherein the scan is carried out by using 2D $^1$H-$^{13}$C HSQC NMR spectroscopy, and
wherein the drug has been approved for use only when the patient has been predetermined as a respond to the drug.

An aspect of the invention includes a method of selecting a population of patients, comprising:
(a) administering to a group of patients a drug over a period of time;
(b) analyzing a metabolite in a biological sample obtained from the patients, the sample is selected from the group consisting of blood, urine, feces, cerebral fluid, saliva and tissue extract of the group of patients at a first point in time;
(c) analyzing the metabolite in a sample of the group of patients at a second point in time different from the first point in time;
(d) comparing results of the analyzing in (b) with the analyzing in (c) to obtain a differential; and
(e) relating the differential to how a patient responds to the drug thereby determining responders to the drug, which are selected for treatment with the drug.

An aspect of the invention may include (f) counseling a patient on how the differential obtained in (d) relates to a patient's likely response to a drug.

An aspect of the invention includes a method of selecting a population of patients, comprising:
(a) analyzing a metabolite in a biological sample selected from the group consisting of blood, urine, feces, cerebral fluid, saliva and tissue extract of the group of patients at a first point in time;
(b) continuing to administer to the group of patients the drug over a period of time;
(c) analyzing the metabolite in the sample of the group of patients at a second point in time different from the first point in time.
(d) comparing results of the analyzing in (a) with the analyzing in (c) to obtain a differential;
(e) relating the differential to how a patient responds to the drug thereby determining responders to the drug, which are selected for further treatment with the drug, wherein the method may further include (f) counseling a patient regarding likelihood of responding to the drug; wherein the drug is an enzyme inhibitor, wherein the drug is selected from the group consisting of CDK4/6 inhibitors palbociclib, ribociclib, anti-her2 drugs, trastuzumab, endocrine therapies, tamoxifen, aromatase inhibitors; and wherein the analyzing is by spectrographic analysis using NMR.

An aspect of the invention includes a determining point at which a patient develops resistant to a drug, comprising:
(a) analyzing a metabolite in a human biological sample of a patient at a first point in time wherein the patient is being treated with a drug;
(b) continuing to treat the patient over time with the drug;
(c) analyzing the sample of the patient at appoint in time different from the analyzing in step (a);
(d) comparing the analyzing of (a) with the analyzing of (c) to obtain a differential; and
(e) relating to differential to a standard in order to determine if the patient has developed a resistance to the rug, and may further include (f) counseling the patient regarding developing resistance to the drug; and discontinuing administration of the drug to the patient when it is determined by comparison of the differential to a standard that the patient has developed resistance to the drug.

An aspect of the invention includes treating a patient, comprising:
(a) analyzing a sample obtained from a patient being treated with a drug using spectroscopy;
(b) obtaining data from the spectroscopy;
(c) comparing the data obtained in (b) with data obtained from a statistically significant sample of patients treated with the same drug in order to determine a differential;
(d) continuing to treat the patient with the drug overtime while periodically repeating steps (a), (b) and (c); and
(e) counseling the patient with respect to the significance of the differential obtained, and
(f) modifying treatment of the patient based on the differential, wherein the patient is a cancer patient, the drug is a cancer drug and the spectroscopy is nuclear magnetic residence (NMR) spectroscopy.

An aspect of the invention further includes analyzing blood components of the patient by obtaining a scan (particularly with NMR spectroscopy) of a blood sample of the patient; and obtaining an array of data on drug metabolite components in the blood of the patient.

Another aspect of the invention includes analysis of blood, comprising scanning a blood component of a patient to determine a match with a metabolic profile of responders to a drug (particularly with NMR spectroscopy).

Another aspect of the invention includes analysis of blood, comprising scanning (particularly with NMR spectroscopy) a blood component of a patient to determine a match with a metabolic profile of responders to a drug; and treating the patient with the drug based on result showing a statistically significant degree of matching the metabolic profile of responders to a drug.

Another aspect of the invention includes analysis of blood, comprising: scanning a blood component (particularly with NMR spectroscopy) of a patient to determine a match with a metabolic profile of responders to a drug; and providing counseling regarding treatments options as a result a statistically significant degree of matching the metabolic profile of responders to a drug.

A method of predicting the responsiveness of a patient to a pharmaceutical drug by measuring metabolites in a biological sample from the patient is disclosed. Metabolites in blood from breast cancer patients are analyzed using NMR spectroscopy. The responsiveness of the human cancer patients before, during and after treatment with CDK4/6 inhibitors palbociclib and ribociclib, anti-Her2 drug trastuzumab, and endocrine therapies tamoxifen and aromatase inhibitors, is assessed by measuring the change in clinical outcomes such as tumor growth, survival and rate of metastasis. Statistical analyses identified particular NMR resonances that are strongly correlated with whether the patient is responsive or resistant to each drug. As such, models for predicting the responsiveness of a patient to each drug based on metabolites from the patient are provided.

A method of determining patient responsiveness to a drug by the use of spectroscopy to obtain patient metabolite data and relating that data to data obtained from a statistically significant group of patients taking the same drug in order to obtain a result indicating responsiveness of a particular patient to treatment with a particular drug.

An aspect of the invention includes analyzing plasma-based metabolites from a baseline (pre-dose) sample women with ER+ early stage BC treated with endocrine therapy, tamoxifen or aromatase inhibitors. By correlating the metabolite expression profiles to clinical outcomes, it is possible to identify a metabolic signature that differentiates the endocrine therapy Responders ("R") and Non-responders ("NW") patients An aspect of the invention is a method of determining patient responsiveness to a drug, comprising:
obtaining a biological sample from the patient that has taken a pharmaceutically active drug; and
analyzing metabolites in the biological sample from the patient;
wherein the biological sample is selected from the group consisting of blood, urine, feces, cerebral fluid, saliva and tissue extract; and wherein the analyzing comprises scanning the biological sample using spectroscopy to obtain data related to metabolites of the drug in the sample, and relating the data to data obtained from a statistically significant group of patients previously administered the same drug.

The spectroscopy may be two-dimensional $^1$H-$^{13}$C heteronuclear single-quantum correlation (HSQC) nuclear magnetic resonance (NMR) spectroscopy and the pharmaceutical drug may be a cyclin-dependent-kinase inhibitor, an anti-HER2 therapy, an endocrine therapy, a metabolic enzyme inhibitor or a drug selected from the group consisting of palbociclib, ribociclib, tamoxifen, aromatase inhibitors, and trastuzumab.

The analyzing step may begin within 4 hours or less after the completion of the obtaining step, within 15 minutes or less after completion of the obtaining step and may include a step wherein the sample is blood, and the blood is put into a tube that contains a preservative and/or freezing.

An aspect of the invention includes a method for determining patient responsiveness to a drug, comprising:
obtaining a sample from a patient before they been administered a drug;
analyzing the sample using spectroscopy to obtain metabolite data on the sample;
relating the data to data obtained with a statistically significant group of patients previously administered the drug, and thereby obtaining information relating to the likelihood of responsiveness of the patient to the drug.

An aspect of the invention includes a method for determining patient responsiveness to a drug, comprising:
obtaining a sample from a patient which patient has been administered a drug;
analyzing the blood sample using spectroscopy to obtain metabolite data in the sample;
relating the data with data obtained with a statistically significant group of patients previously administered the same drug, and thereby obtaining information relating to the responsiveness of the patient to the drug, which method may be carried out wherein the drug is selected from the group consisting of:
palbociclib;
ribociclib;
tamoxifen;
aromatase inhibitors; and
trastuzumab.

An aspect of the invention includes a method of counseling a patient, comprising:
analyzing a sample obtained from a patient treated with a drug using spectroscopy to obtain patient data;
comparing the patient data to data obtained from a statistically significant group of patients treated with the same data to obtain a differential;
counseling the patient on significance of the differential, which method may also include:
repeating the above steps over time as the patient is treated with the drug; and
determining drug resistance, which method may be wherein the patient is a cancer patient, the drug is a cancer drug and the spectroscopy is nuclear magnetic resonance (NMR) spectroscopy.

These and other aspects, objects, advantages, and features of the invention will become apparent to those persons skilled in the art upon reading the details of the methodology as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2B. Shows violin plots of the top NMR grids that had largest difference in signal between CDK4/6 R and NR patients from a baseline plasma sample.

FIG. 3. Describes the metabolites and metabolite resonances associated with CDK4/6 Intrinsic Resistance FIG. 4A. Shows violin plots of the top NMR grids that had largest difference in signal between palbociclib R vs NR from a baseline plasma sample FIG. 4B. Shows violin plots of the top NMR grids that had largest difference in signal between ribociclib R vs NR from a baseline plasma sample FIG. 5A. Shows volcano plot comparing metabolite grids for CDK4/6 R vs NR from a two-month post treatment plasma sample FIG. 5B. Shows volcano plot comparing metabolite grids for CDK4/6 R vs NR from a two-month post treatment plasma sample FIG. 6. Describes the metabolites and metabolite resonances associated with CDK4/6 Acquired Resistance FIG. 7. Shows Progression Free Survival for HER2+ metastatic breast cancer patients treated with trastuzumab FIG. 8A. Shows volcano plot comparing metabolite grids for trastuzumab R vs NR from a baseline serum sample.

FIG. 9. Describes the metabolites and metabolite resonances associated with Trastuzumab Resistance FIG. 10A. Shows volcano plot comparing metabolite grids for ET R vs NR from a baseline plasma sample.

FIG. 11. Describes the metabolites and metabolite resonances associated with ET Resistance

DETAILED DESCRIPTION OF THE INVENTION

Figure 1A:
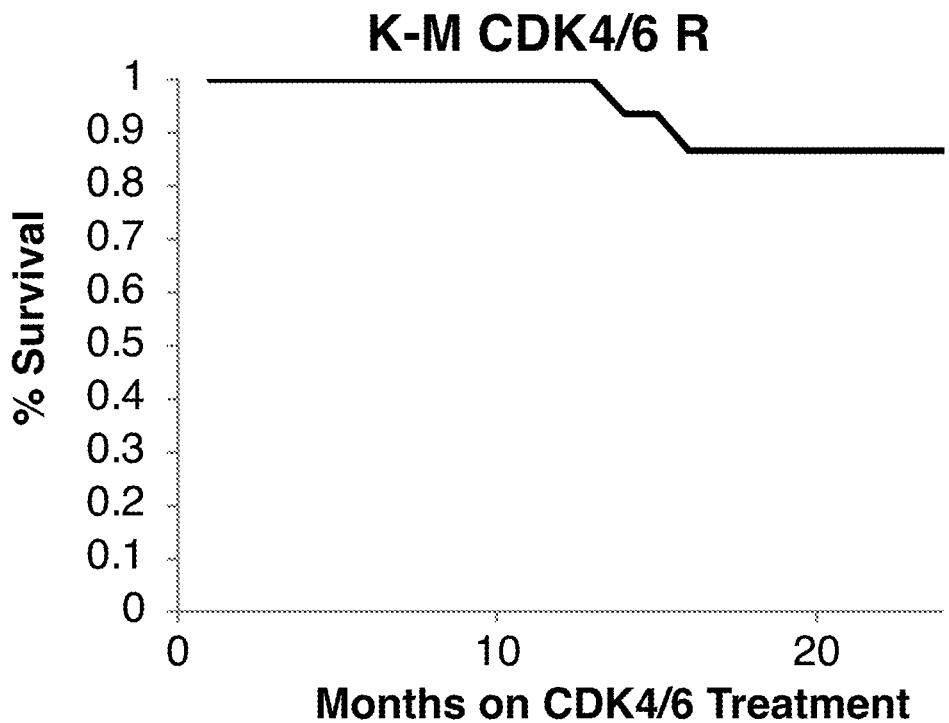
FIG. 1A. Shows the Kaplan-Maier survival curve for CDK4/6 Responder ("R") patients.

Before the present methods and uses are described, it is to be understood that this invention is not limited to particular steps, devices and compounds described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a scan" includes a plurality of such scans and reference to "the Biomarker of Response" includes reference to one or more such Biomarkers of Response and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "biomarker of response (BoR)" is broadly used herein to describe any detectable signal which can be related to a patient's probability of being responsive to or resistant to a drug. A biomarker of response may be a spectrographic scan, an array of data, or analysis of a group of scans or data points which have been determined to show a probability that a patient will be either responsive to or resistant to treatment with a drug. The biomarker of response may be an endogenous metabolite(s), microbiome metabolite(s), xenobiotic(s), drug metabolite(s) or a combination thereof determined to exist in the patient by itself or in a particular amount after a particular point in time as measured from the administration of a particular dose of the drug.

Spectroscopy

Nuclear magnetic resonance spectroscopy, most commonly known as NMR spectroscopy or magnetic resonance spectroscopy (MRS), is a spectroscopic technique to observe local magnetic fields around atomic nuclei. The sample is placed in a magnetic field and the NMR signal is produced by excitation of the nuclei sample with radio waves into nuclear magnetic resonance, which is detected with sensitive radio receivers. The intramolecular magnetic field around an atom in a molecule changes the resonance frequency, thus giving access to details of the electronic structure of a molecule and its individual functional groups. As the fields are unique or highly characteristic to individual compounds which include drugs and their metabolites, in modern organic chemistry practice, NMR spectroscopy is the definitive method to identify monomolecular organic compounds. Similarly, biochemists use NMR to identify proteins and other complex molecules. Besides identification, NMR spectroscopy provides detailed information about the structure, dynamics, reaction state, and chemical environment of molecules. The most common types of NMR are proton and carbon-13 NMR spectroscopy, but it is applicable to any kind of sample that contains nuclei possessing spin.

The types of spectroscopy also can be distinguished by the nature of the interaction between the energy and the material. These interactions include:

Absorption spectroscopy: Absorption occurs when energy from the radiative source is absorbed by the material. Absorption is often determined by measuring the fraction of energy transmitted through the material, with absorption decreasing the transmitted portion.

Emission spectroscopy: Emission indicates that radiative energy is released by the material. A material's blackbody spectrum is a spontaneous emission spectrum determined by its temperature. This feature can be measured in the infrared by instruments such as the atmospheric emitted radiance interferometer. Emission can also be induced by other sources of energy such as flames or sparks or electromagnetic radiation in the case of fluorescence.

Elastic scattering and reflection spectroscopy determine how incident radiation is reflected or scattered by a material. Crystallography employs the scattering of high energy radiation, such as x-rays and electrons, to examine the arrangement of atoms in proteins and solid crystals.

Impedance spectroscopy: Impedance is the ability of a medium to impede or slow the transmittance of energy. For optical applications, this is characterized by the index of refraction.

Inelastic scattering phenomena involve an exchange of energy between the radiation and the matter that shifts the wavelength of the scattered radiation. These include Raman and Compton scattering.

Coherent or resonance spectroscopy are techniques where the radiative energy couples two quantum states of the material in a coherent interaction that is sustained by the radiating field. The coherence can be disrupted by other interactions, such as particle collisions and energy transfer, and so often require high intensity radiation to be sustained. Nuclear magnetic resonance (NMR) spectroscopy is a widely used resonance method, and ultrafast laser spectroscopy is also possible in the infrared and visible spectral regions.

The term "sample or biological sample" refers to any material extracted from a living plant or animal and includes blood, urine, feces, cerebral fluid, saliva and tissue which may be tissue from a tumor.

Preservation Step

In some embodiments, the method includes preserving the biological sample before it is analyzed. Methods are known in the art for preserving a biological sample, such as introducing blood into a tube that contains at least one preservative. Tubes that contain a preservative are known and described in the art, such as in U.S. Pat. Nos. 7,419,832 and 7,608,457, which are incorporated herein by reference to disclose and describe sample collection tubes and methods of use. The preservative can be an anticoagulant, an antimicrobial, a surfactant, a combination thereof, or other preservative. The preservative can be a liquid, solid, gas, gel, cream, paste, or other form. Examples of preservatives are described in U.S. Patent Application No. 2004/0137417 and Annex E of ISO 6710: 1995(E) for "Single-use containers for venous blood specimen collection", which are incorporated herein by reference to disclose and describe such preservatives. In other embodiments, the preservation step can include changing the temperature of the sample, such as lowering the temperature of the sample. The temperature of the sample can be lowered so that the sample is frozen, e.g., by using liquid nitrogen or dry ice. In some embodiments, more than one preservation method can be used. By preserving the sample, the results of the analysis of a sample can be improved relative to the results of analysis of a sample that was not preserved. As used herein, preserving a sample means that changes in the sample over time are reduced or eliminated when compared to a sample that was not preserved. Preserving a sample is not limited to methods that maintain a sample in its original state for an indefinite period of time.

In other embodiments the analysis of the sample is begun within a certain period of time after the sample was obtained. Such a period of time can be 1 second, 15 seconds, 30 seconds, 1 minute, 5 minutes, 15 minutes, 30 minutes, 45 minutes, 60 minutes, 2 hours, 4 hours, 6 hours, 24 hours, 72 hours, or a longer or shorter period of time. By beginning the analysis of the sample within a certain period of time after the sample was obtained the results of the analysis of the sample can be improved relative to the results of analysis of a sample where a longer period of time elapsed before analysis of the sample was begun. In some embodiments, the sample can be preserved and the analysis of the sample can be begun within a certain period of time after the sample was obtained. Analysis of the sample after a set period of time following extraction of the sample makes it possible to more meaningfully compare the results obtained to a standard.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

CDK4/6 BoR R Vs NR

One in 8 women are likely to develop breast cancer (BC) in her lifetime. Early detection and access to new-targeted therapies has improved the overall survival for localized cases. However, metastatic breast cancer (mBC) remains incurable with only 22% of patients surviving 5-years post diagnosis. Recently, 3 relatively selective CDK4/6 inhibitors (palbociclib, ribociclib, and abemaciclib) have demonstrated clinical utility as mBC treatments. These drugs significantly extended progression-free survival (PFS) when used as first-line or later therapy for horomone receptor positive (HR+), human epidermal growth factor negative (HER2−) mBC patients. However about 20% of patients are intrinsically resistant (IR) to these therapies and all patients ultimately acquire resistance (AR). Thus, there is a critical need to identify biomarkers to more accurately predict patient response and resistance to CDK4/6 inhibitors. Further, because palbociclib, ribociclib and abemaciclib, show differential relative potency for CDK4/6, as well as distinct pharmacokinetic and toxicity profiles, it is also of utmost importance to determine if distinct response and/or resistance profiles exist for specific drugs.

Tremendous efforts are underway to uncover these biomarkers. Currently these drugs are approved only for ER+ breast cancer. However, in a phase 1 study of abemaciclib monotherapy, only 11 of 36 ER+ patients experienced clinical benefit. Further in PALOMA-2 and PALOMA-3 trials, benefit from palbociclib did not differ by ER IHC expression. High levels of cyclin D and/or low levels of p16 have also been postulated as biomarkers, however in a phase II study of palbociclib, and the phase II PALOMA-1 study neither cyclin D nor p16 amplification was predictive of clinical benefit. Utilizing BC cell line models, different studies have suggested the CDK4/6 inhibitors are more effective in luminal BCs, less sensitive in cell lines with low levels of Rb mRNA and overexpression of CDK2 has been reported as a CDK4/6 inhibitor escape mechanism. These in vitro studies have not been clinically validated.

To date, nearly all of the CDK4/6 biomarker efforts have utilized genomics (DNA or RNA). Genomics delivers powerful insight, relying what "could happen" in a patient. Metabolites, small molecules providing energy and biomass, are an additional class of biomarkers, that reveal "what is happening" in a patient. A patient's metabolic output is determined by the genome and the environment (including diet, xenobiotics and the microbiome). We hypothesized metabolite biomarkers may be able to more accurately predict patient response and resistance to CDK4/6 inhibitors.

Here we describe a retrospective study analyzing plasma-based metabolites from a baseline (BL) sample and after 2-months (2M) of treatment of 24 women with ER+/HER2−− metastatic BC treated with CDK4/6 inhibitors, palbociclib or ribociclib. By correlating the metabolite expression profiles to clinical outcomes we were able to identify a metabolic signature that could differentiate the CDK4/6 responders ("R") and CDK4/6 non-responders ("NR"). Further, we were also able to identify separate signatures of response and resistance specific to palbociclib and ribociclib. The results of this study could lead to a paradigm shift in the administration of CDK4/6 inhibitors wherein prior to and during treatment patient plasma is screened to determine 1) the likelihood an individual patient is a CDK4/6 R or NR, 2) which CDK4/6 inhibitor will be most appropriate and 3) to monitor if that therapy remains effective or not for that individual patient.

Plasma Preparation:

Whole blood from patients was collected in cell-free DNA BCT tubes (Streck) and spun at 16,000 RCF to isolate the plasma at ambient temperature. Plasma was re-centrifuged at 3000 RCF at ambient temperature, separated into 1 mL aliquots and stored at −80° C.

Metabolite Extraction:

Plasma aliquots were thawed on ice and cleared via precipitation with ice-cold methanol (1:2 ratios v/v), vortexed, incubated −20° C. overnight, and centrifuged at 13,400 rcf for 30 min at 4° C. to pellet proteins. The supernatant was collected and dried overnight in a speed vac.

NMR Preparation & Analysis:

Dried metabolic extracts were resuspended in 200 μL of phosphate buffer (pH 7.4) in $D_2O$ containing 1 mM DSS and transferred to 3 mm NMR tubes. All samples were stored at 4° C. until analysis. 1D-$^1$H NMR and 2D $^1$H-$^{13}$C heteronuclear single quantum coherence spectroscopy (HSQC) spectra were collected on a Bruker 600 MHz spectrometer equipped with a cryoprobe. NMR data were processed using NMRPipe and proprietary Olaris software.

Statistics and Machine Learning:

A Wilcoxon non-parametric one-way analysis of variance was used to test for significant differences in measured metabolite resonances. Significantly altered or differentially expressed resonances were identified based on p-value<0.05. Subsequent analysis was limited to significantly altered variables. Non-supervised clustering techniques were used to visualize similarities between samples. To further discriminate samples, we implored predictive modeling and machine learning algorithms.

Characteristics of Patients and Survival Analysis of CDK4/6 R Vs. NR

Figure 1B:
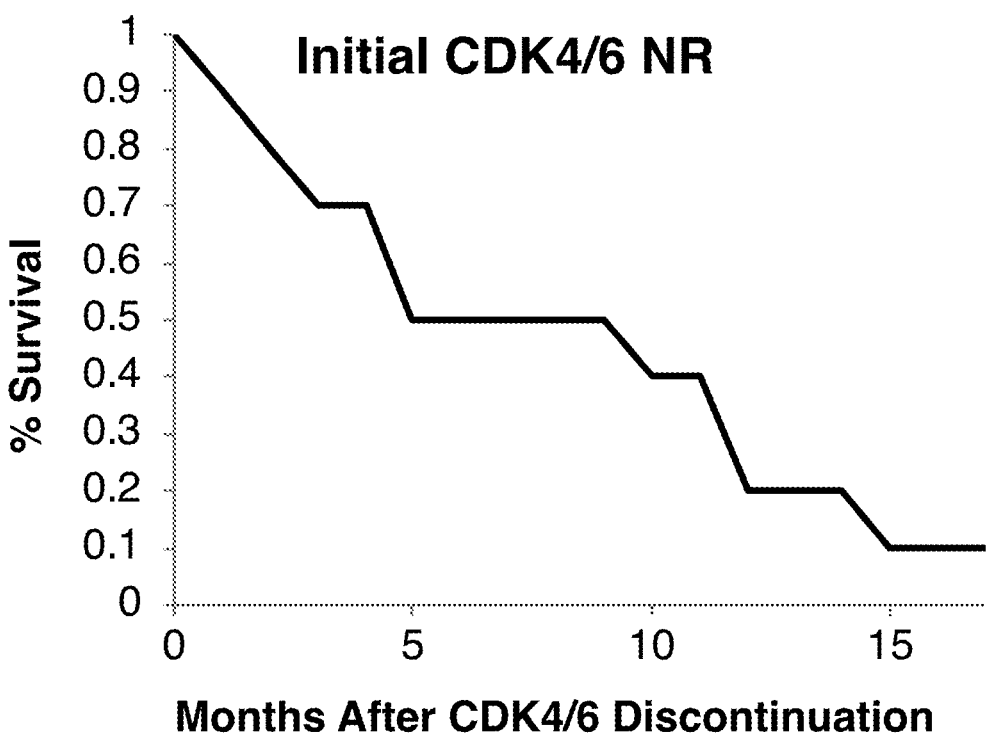
FIG. 1B. Shows the Kaplan-Maier survival curve for CDK4/6 Non-Responder ("NW") patients.

Patients with at least a 30% decrease in the sum of diameters of target tumors after 6 months of treatment were classified as a "responder" (R), while the "non-responders" (NR) were those patients that displayed at least a 20% increase in the sum of diameters of target tumors after 6 months. Ten patients (42%) were categorized as CDK4/6 NR. Within the NR group 3 patients received palbociclib and 7 patients received ribociclib. FIG. 1A-B shows the corresponding Kaplan-Maier survival curves for the overall survival (OS) in CDK4/6 R and CDK4/6 NR patients. Twelve out of 14 of the CDK4/6 R patients (86%) remain alive after 24 months. In stark contrast, despite halting CDK4/6 treatment and administering alternative lines of therapy, only 1 out 10 CDK4/6 NR patients (10%) survived beyond 15 months of switching therapy.

CDK4/6 R Vs. NR Display Significantly Different Baseline Metabolite Resonances

Many metabolites are liable. Streck plasma collection tubes contain a proprietary mixture of preservatives designed to stabilize nucleated blood cells for genomic analysis. We hypothesized the preservatives would inactivate metabolic enzymes increasing metabolite stability. Indeed, when comparing plasma metabolites from the same patient isolated from Streck tubes and EDTA-containing tubes, an increase in the number of metabolite resonances was observed in samples derived from the Streck tube. The preservatives in the Streck tubes did contribute resonances to the NMR spectrum which were eliminated in the analysis.

Figure 2A:
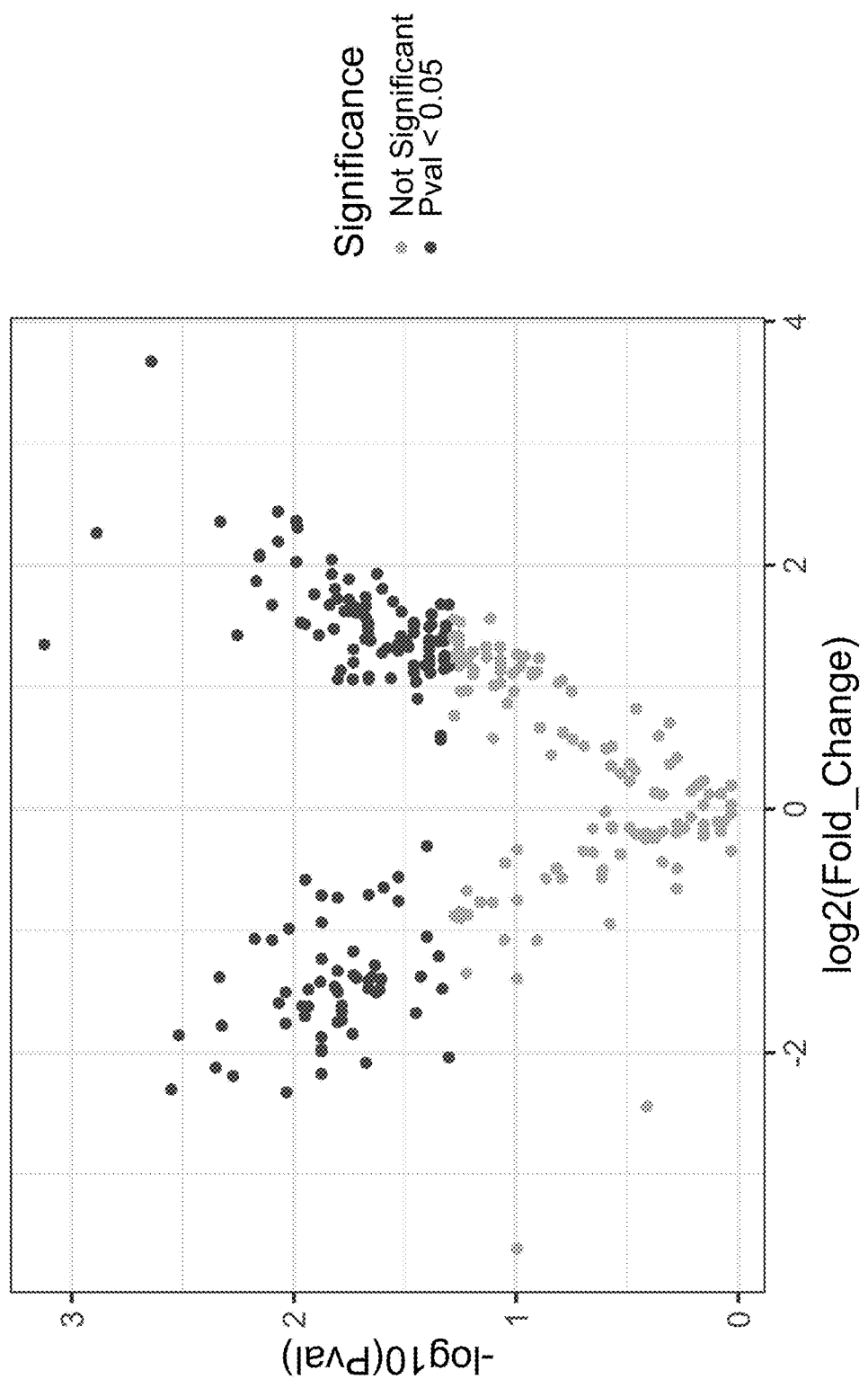
FIG. 2A. Shows volcano plot comparing metabolite grids for CDK4/6 R vs NR from a baseline plasma sample.

To gain a better understanding of the metabolite differences between R vs NR, we applied a "grid system" with a grid size of 0.25 ppm by 0.9 ppm in the $^1$H and $^{13}$C direction respectively across all spectra. Using the Wilcoxon test for significance, 148 grids differed between R and NR baseline samples with a p-value of less than 0.05, shown in FIG. 2A. Only 14 grids were expected by chance, suggesting the 148 differences observed between R vs NR are biologically significant. Violin plots for the top statistically different grids are shown in FIG. 2B. Many metabolite resonances are higher in the R patients and lower in the NR patients or vice versa. For example, Grid #2750 (centered at 3.75 ppm in $^1$H and 71.1 ppm in $^{13}$C) and Grid #2225 (centered at 3.0 ppm in $^1$H and 79.2 ppm in $^{13}$C), provide examples of metabolite resonances significantly enriched in NR or R patients respectively (FIG. 2B).

BoR to Detect CDK4/6 Intrinsic Resistance

To uncover putative diagnostic features to discriminate R vs. NR we implored a series of statistical methods including principle component analysis (PCA), orthogonal partial least squares discriminate analysis (OPLS-DA), random forest (RF), support vector machines (SVM) with radial kernel, SVM with linear kernel, generalized linear model, and glmnet. Combining the top features from all models, we identified a signature of metabolite resonances that was able to perfectly differentiate the CDK4/6 NR patients. The metabolites and/or metabolite resonances that identify CDK4/6 NR patients are listed in FIG. 3. A subset of these metabolites were validated using mass-spectrometry. The relative expression of these metabolites and/or metabolite resonances could be used to screen future mBC patients to determine CDK4/6 response and resistance.

Independent BoR Scores for Palbociclib and Ribociclib

Figure 4B:
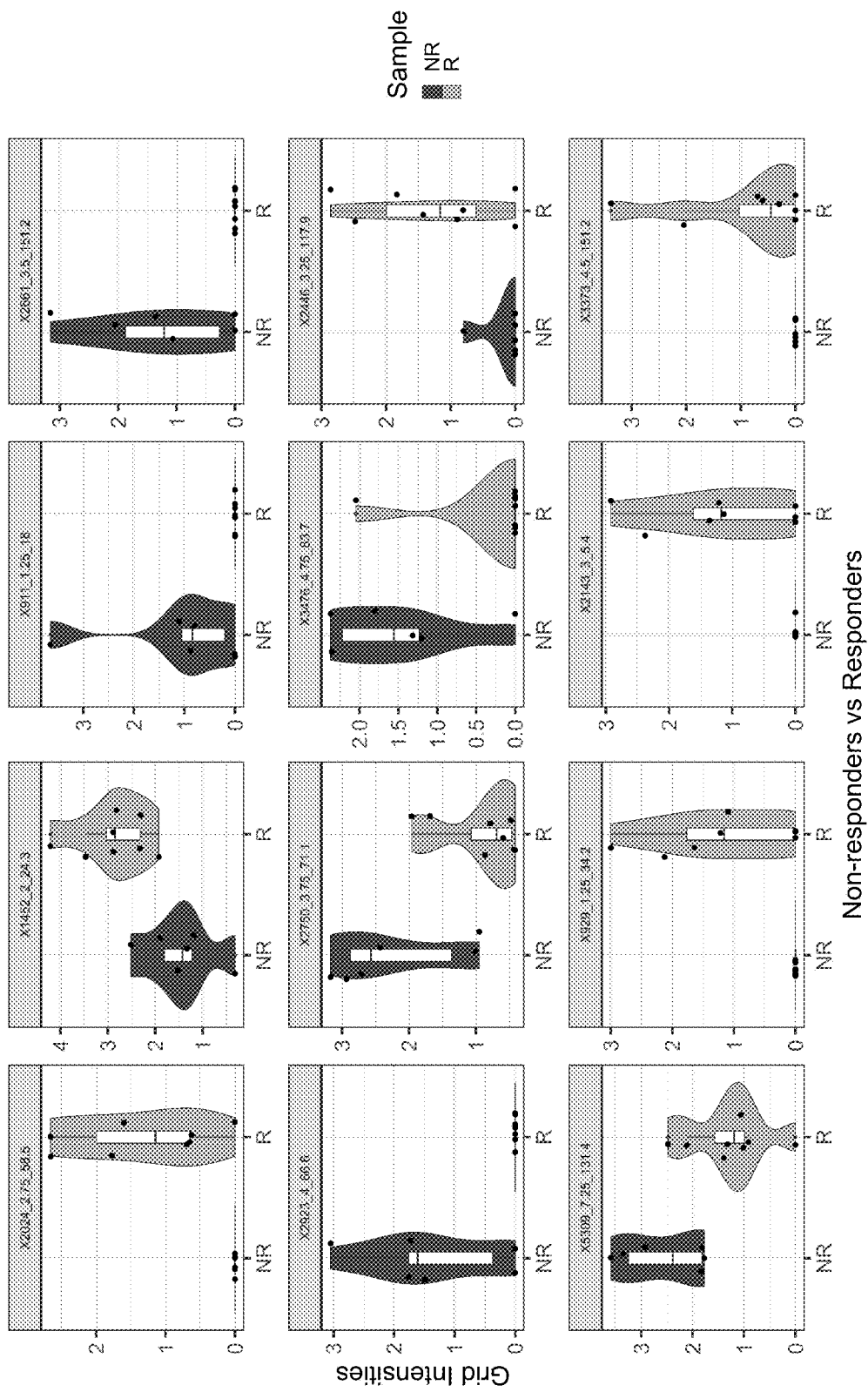

To test for drug-specific distinctions, we repeated our analysis separating the samples based on inhibitor, palbociclib (N=10, R=7, NR=3) and ribociclib (N=14, R=8, NR=6). The number of significantly different metabolite resonance grids between R vs. NR for each drug was 150 for palbociclib and 36 for ribociclib. The top significantly different metabolites between R vs NR differed for palbociclib and ribociclib are shown in FIGS. 4A and 4B respectively. For palbociclib, there were several metabolite resonances that were only present in the NR patients and completely absent in the R patients (FIG. 4A). The simple presence of any one of these metabolites could be used to exclude patients from palbociclib as they suggest resistance to this drug. The majority of metabolites that differentiate palbociclib and ribociclib R vs NR are different. This data refutes the current notion that palbociclib and ribociclib are interchangeable and instead suggests specific patients are more likely to benefit from one or the other therapy. These metabolites could be used to screen future mBC patients to determine which, if any, CDK4/6 treatment is the most optimal.

BoR to Detect Acquired Resistance

Figure 5A:
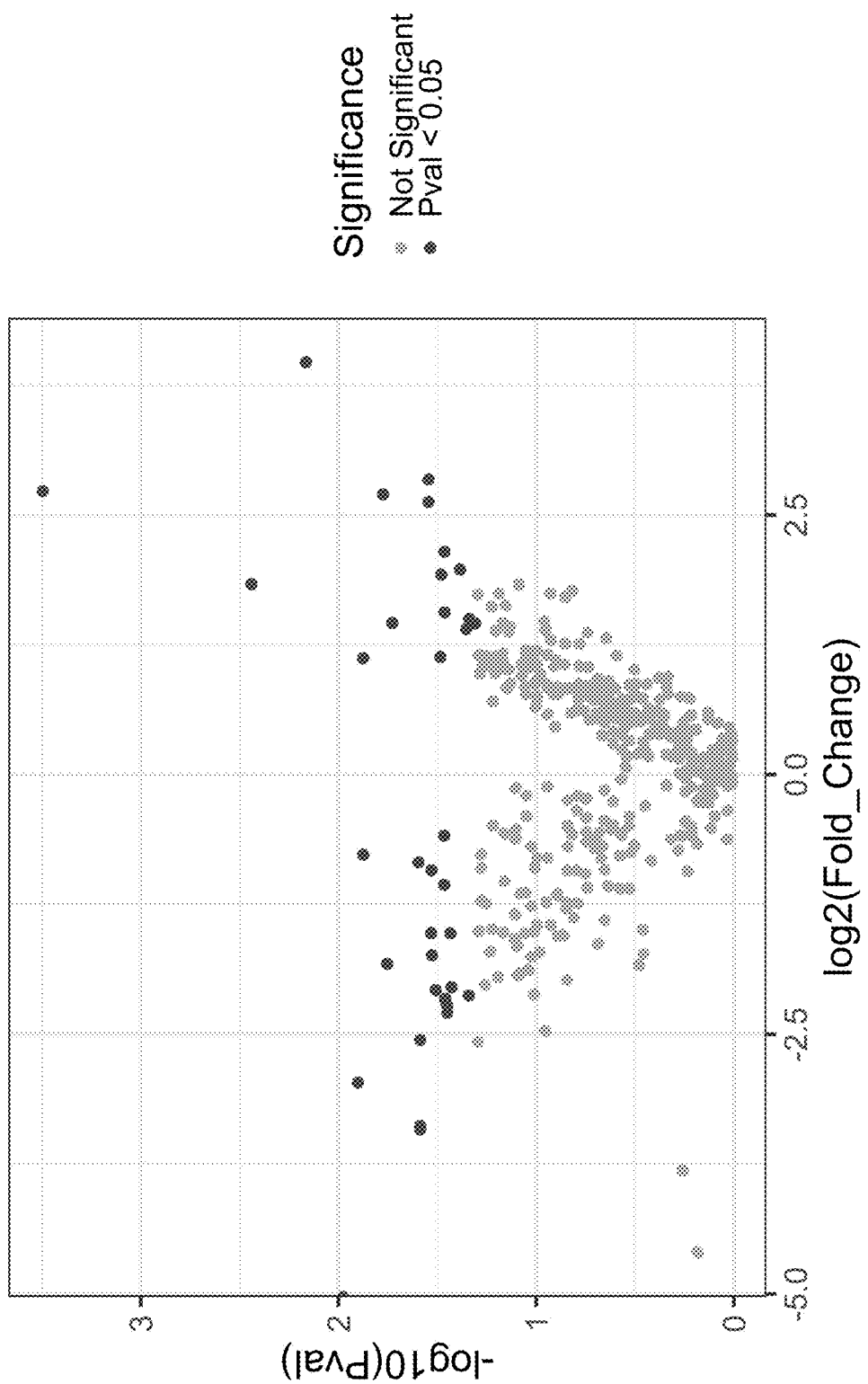

All breast cancer patients eventually acquire resistance to CDK4/6 inhibitors. Being able to detect acquired resistance (AR) at its earliest onset would allow physicians to halt ineffective treatment in place of subsequent lines of therapy. Acquired resistance usually develops after ~1-2 years of CDK4/6 inhibitor treatment. To gain insight into the metabolites influenced by CDK4/6 treatment we analyzed an on-treatment metabolite plasma sample after approximately 2 months of treatment ("2M sample") from the same 24 patients. We identified 37 metabolite resonance grids that differed between R and NR patients at this time point shown in FIG. 5A. Only 21 grids were expected by chance, suggesting the 37 differences observed between R vs NR are biologically significant. The top statistically different metabolite grids are shown in FIG. 5B.

To determine if a metabolite-based BoR for acquired resistance could be developed, again we used a series of statistical methods including PCA, OPLS-DA, RF, SVM with linear kernel, generalized linear model, and CART. Combining the top features from all models, we identified a signature of metabolite resonances that was able to perfectly differentiate the CDK4/6 R and NR patients. The metabolites and/or metabolite resonances that differentiate CDK4/6 R vs NR patients at 2M-post treatment are listed in FIG. 6.

Only one of these metabolite resonance grids matched with the baseline BoR model. This suggests there is a separate on-treatment signature able to differentiate CDK4/6 R vs NR. The relative expression of these metabolites and/or metabolite resonances could be used to screen future mBC patients for CDK4/6 acquired resistance during treatment.

Example 2

Trastuzumab BoR R Vs NR

Cancer cells have altered metabolism, which contributes to their ability to proliferate, survive in unusual microenvironments, and invade other tissues. Measuring the complete set of metabolites in an individual (ie the metabolome) provides a functional readout for cellular pathways. Further, changes in the metabolome can be correlated with disease status, prognosis and progression. Using a metabolomics platform and machine learning algorithms, biomarker signatures can be identified to predict response to therapy.

Breast cancers are classified based on increased expression of cell-surface receptors including the tyrosine-protein kinase HER2/neu (Her2+), estrogen receptors (ER+) and progesterone receptors (PR+). Approximately 20% of breast tumors are characterized as HER2+. The HER2 gene is an oncogene and its amplification is believed to drive tumor growth. This has led to the development of several anti-HER2 therapies which shut down HER2-signaling pathways. Trastuzumab (manufactured under the brand name Herceptin), a monoclonal antibody that binds to the HER2 receptor inhibiting dimerization and thus downstream activation of the HER2-pathway, was the first therapy available to clinicians and HER2+ breast patients. Additional anti-HER2 therapies such as palatinib, pertuzumab, neratinib and TDM1 have followed.

These targeted therapies have impressively improved HER2+ breast cancer prognosis. However, efficacy of individual anti-HER2 therapies is short-lived, wherein approximately 75% of patients relapse within 12 months. Intrinsic and acquired resistance leads to treatment failure. HER2+ metastatic breast cancer remains a deadly disease.

The median progression free survival (PFS) for trastuzumab is approximately 1 year, after which the therapy is no longer effective. Several resistance mechanisms have been identified such as impaired drug binding to HER2 through receptor variants or molecular masking, constitutive activation of signaling pathways parallel or downstream of HER2 such as CDK4/6-CyclinD, PI3K, AKT, and mTOR pathways, or reduced immune system activation such as escape from antibody-dependent cellular cytotoxicity (ADCC). Overexpression of Fatty Acid Synthase gene (FASN) has also been associated with poor clinical response to anti-Her2 therapy. Unfortunately, few of these biomarkers have been clinical validated.

Here we retrospectively evaluated the pretreatment serum metabolome for association with PFS in a cohort of 23 trastuzumab-treated metastatic breast cancer patients. We were able to identify a metabolite signature that perfectly differentiated patients who had a durable response to trastuzumab (PFS>301 days) compared to those with early relapse to treatment (PFS<301 days). This metabolite BoR could be used to screen future patients to predict response to trastuzumab. Further, by identifying the metabolites and metabolic pathways that differ between early and late progressors, our results could lead to novel targets and/or suggest combination treatments in the HER2+ breast cancer setting.

Sample Characteristics:
Pretreatment serum was collected from 23 HER2+ trastuzumab-naive metastatic breast cancer patients who would go onto to be treated with trastuzumab and chemotherapy.

Metabolite Extraction:
Plasma aliquots were thawed on ice and cleared via precipitation with ice-cold methanol (1:2 ratios v/v), vortexed, incubated −20° C. overnight, and centrifuged at 13,400 rcf for 30 min at 4° C. to pellet proteins. The supernatant was collected and dried overnight in a speed vac.

NMR Preparation & Analysis:
Dried metabolic extracts were resuspended in 200 µL of phosphate buffer (pH 7.4) in $D_2O$ containing 1 mM DSS and transferred to 3 mm NMR tubes. All samples were stored at 4° C. until analysis. 1D-$^1$H NMR and 2D $^1$H-$^{13}$C heteronuclear single quantum coherence spectroscopy (HSQC) spectra were collected on a Bruker 600 MHz spectrometer equipped with a cryoprobe. NMR data were processed using NMRPipe and proprietary Olaris software.

Statistics and Machine Learning:
A Wilcoxon non-parametric one-way analysis of variance was used to test for significant differences in measured metabolite resonances. Significantly altered or differentially expressed resonances were identified based on p-value<0.05. Subsequent analysis was limited to significantly altered variables. Non-supervised clustering techniques were used to visualize similarities between samples. To further discriminate samples we implored predictive modeling and machine learning algorithms.

Progression Free Survival Analysis of Trastuzumab R vs NR

The PFS for 23 HER2+ mBC patients treated with trastuzumab and chemotherapy is shown in FIG. 7. The median PFS for this cohort was 301 days (dotted line), which correlates with previous reports of trastuzumab median PFS at approximately 1 year. Patients were subdivided into early progressors (PFS<301 days) and late progressors (PFS≥301 days). The late progressors had a durable response to trastuzumab and thus were defined as trastuzumab "Responders" (R, N=10) and the early progressor patients, who had significantly less benefit from the drug, were defined as trastuzumab "Non-responders" (NR, N=13). Sixteen of the 23 patients received trastuzumab as part of first line therapy, including 9 NR and 7 R patients. The remaining patients received trastuzumab as part of second-, third-, fourth-line or beyond.

Figure 8A:
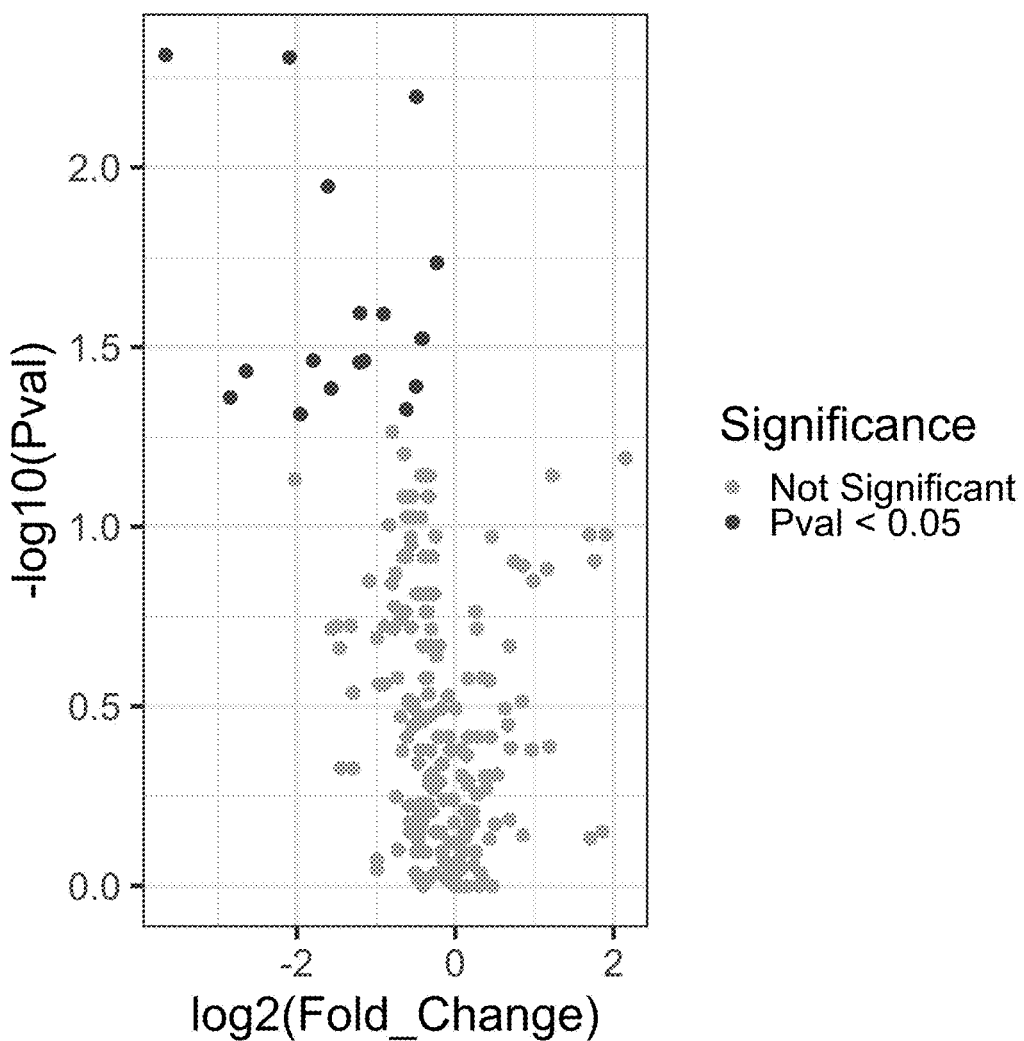
FIG. 8B. Shows volcano plot comparing metabolite grids for first-line treated trastuzumab R vs NR from a baseline serum sample.
FIG. 8C. Shows violin plot of the top NMR grids that had largest difference in signal between trastuzumab R and NR patients from a baseline serum sample.
FIG. 8D. Shows violin plot of the top NMR grids that had largest difference in signal between first-line treated trastuzumab R and NR patients from a baseline serum sample.
Figure 8B:
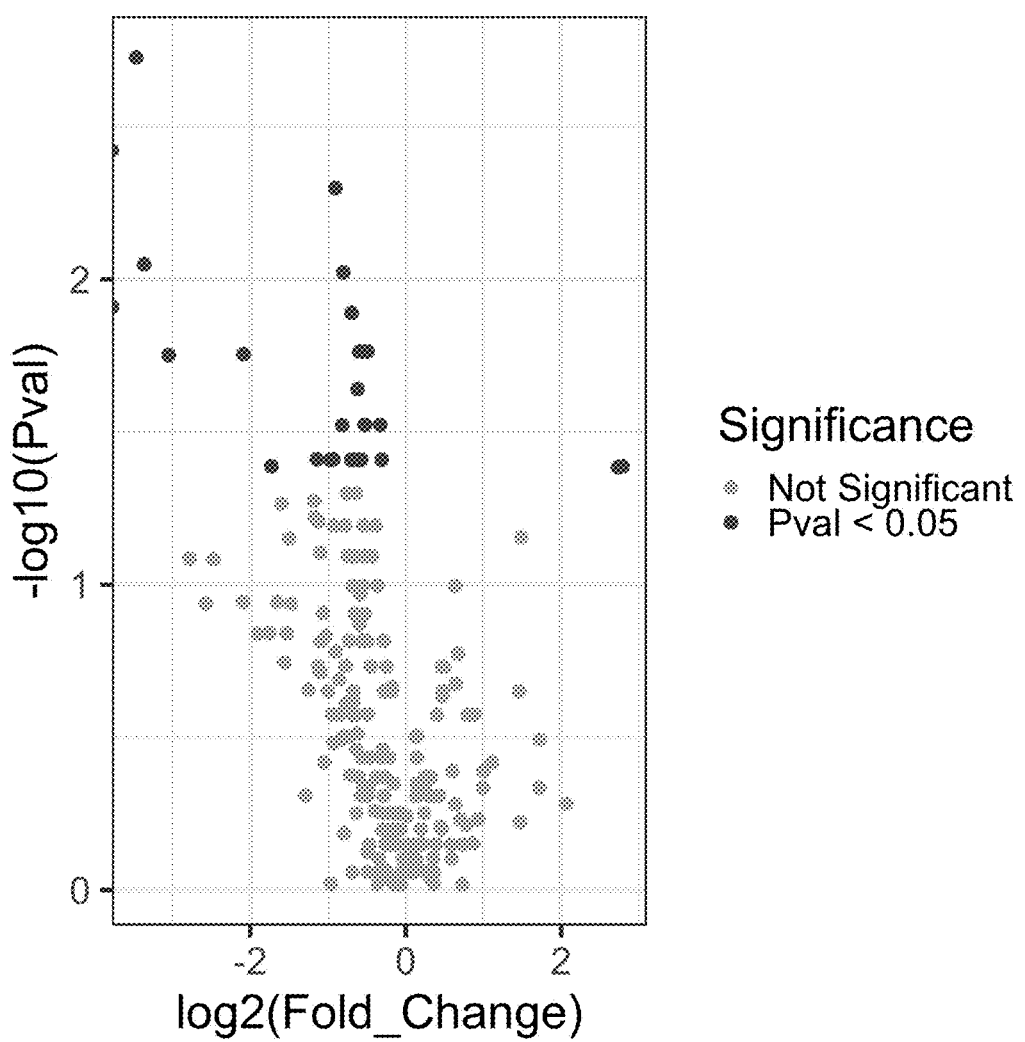
Figure 8C:
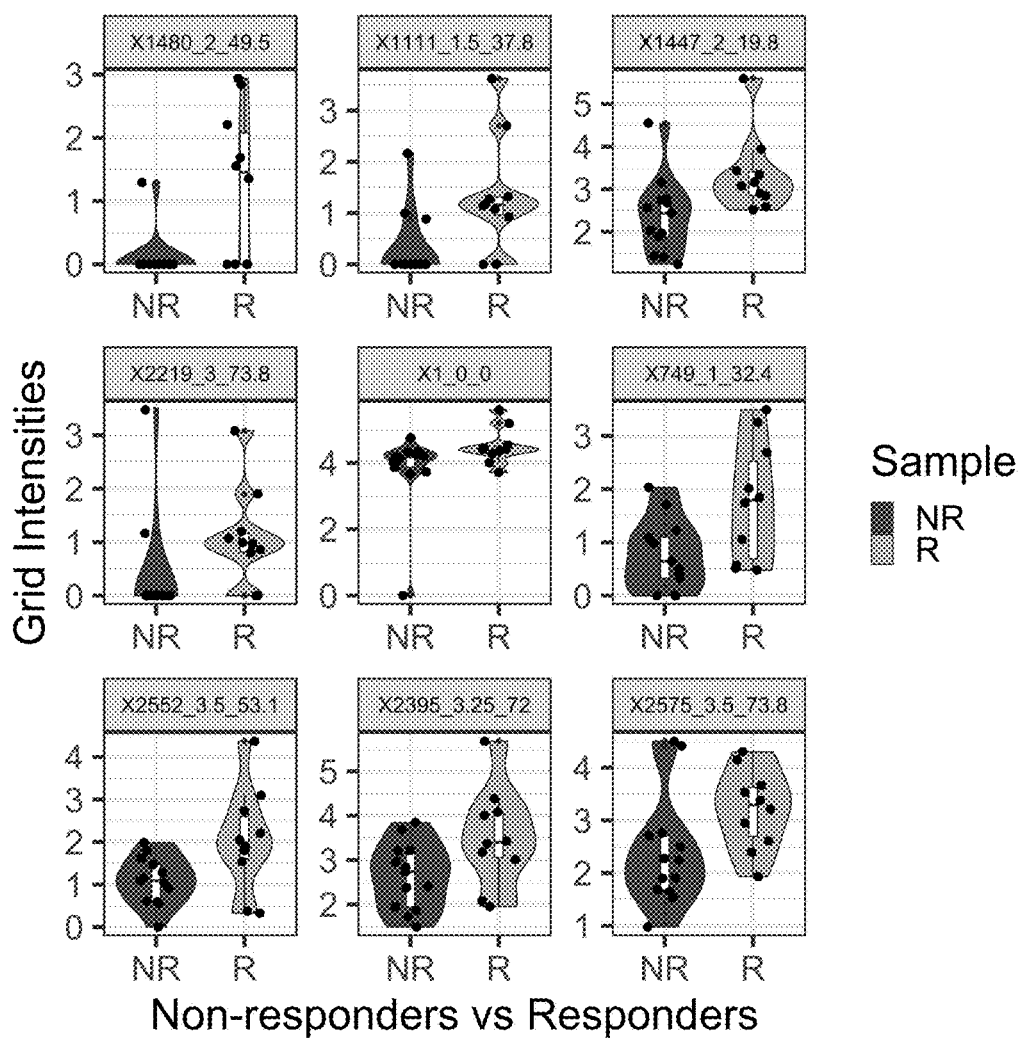
Figure 8D:
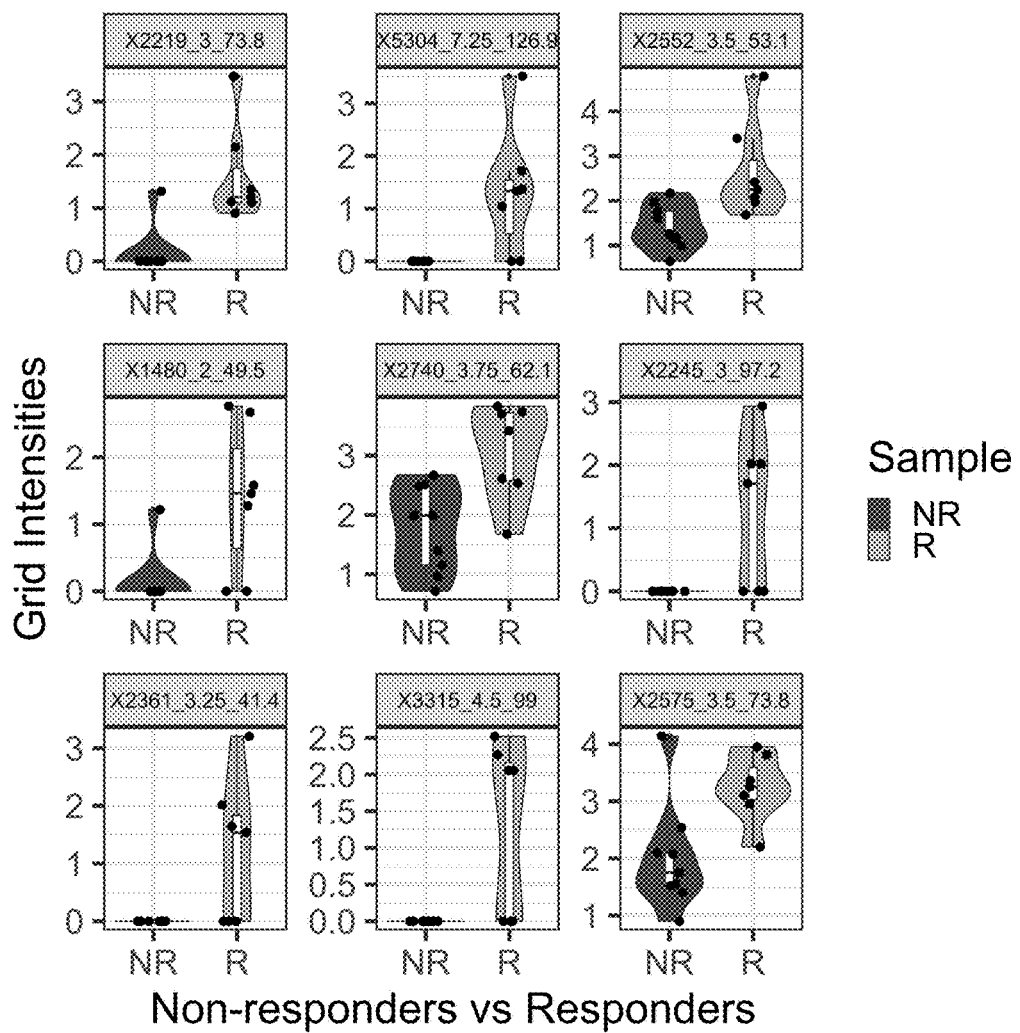

Trastuzumab R Vs NR Display Significantly Different Baseline Metabolite Resonances To gain a better understanding of the metabolite differences between R vs NR, we applied a "grid system" with a grid size of 0.25 ppm by 0.9 ppm in the $^1$H and $^{13}$C direction respectively across all spectra. Using the Wilcoxon test for significance, 18 grids differed between R and NR with a p-value of less than 0.05, shown in FIG. 8A. When we repeated the analysis with the subset of patients who received trastuzumab as part of first line therapy only we identified 29 grids that differed between NR and R patients shown in FIG. 8B. Only 11 grids were expected by chance, suggesting the differences observed between R vs NR are biologically significant. Violin plots for the top statistically different grids for both analysis are shown in FIG. 8C-D. Many of the grids overlapped between both analysis. Future analysis focused on these grids.

BoR to Detect Trastuzumab Intrinsic Resistance

To uncover putative diagnostic features to discriminate R vs. NR we implored a series of statistical methods including principle component analysis (PCA), orthogonal partial least squares discriminate analysis (OPLS-DA), random forest (RF), naïve bayes, support vector machines (SVM) with radial kernel, SVM with linear kernel, generalized linear model, and CART. Combining the top features from all models, we identified a signature of metabolite resonances that was able to perfectly differentiate the trastuzumab R and NR patients. The metabolites and/or metabolite resonances that differentiate trastuzumab R and NR patients are listed in FIG. 9. A subset of these metabolites were validated using mass-spectrometry. The relative expression of these metabolites and/or metabolite resonances could be used to screen future HER2+ mBC patients to predict duration of response to trastuzumab.

Example 3

Endocrine Therapy (ET) BoR R Vs NR

ER+ is the most common clinical subtype of BC, characterized by increased expression of the estrogen cell-surface receptor, encoded by the ESR1 gene and comprising ~80% of breast cancer patients. ER+ breast cancers are often dependent on estrogen for growth. Targeted therapies known as endocrine therapies (ET) have been developed for this breast cancer subtype. ETs include ER modulators, such as tamoxifen, that inhibit estrogen binding to the estrogen receptor, estrogen down regulators, such as fulvestrant, that accelerate degradation of the estrogen receptor and aromatase inhibitors (AIs), such as letrozole, anastrozole and exemestane, that inhibit the enzyme that catalyzes the conversion of androgens to estrogens. Collectively these ETs lead to decreased estrogen signaling and/or estrogen levels and have been demonstrated to block estrogen-dependent tumor growth in vitro and in vivo.

However, the effectiveness of ET is severely reduced by intrinsic or acquired resistance. Resistance manifests in 30-50% of early stage breast cancer patients treated with ET. In the metastatic setting nearly half of the patients experience intrinsic resistance while the remainder develop acquired resistance during therapy. ET-resistant tumors can remain dormant for more than 20 years before the onset of metastasis. These resistant tumors are the main cause of death for breast cancer patients.

An increasing number of ET resistance mechanisms have been reported. This includes changes in ESR1 expression, ESR1 mutations, alternative splicing events, ESR1 truncation and fusion events, post-translational modifications to the estrogen receptor protein, alterations in the hormone binding domain of the receptor, differential recruitment of coregulators, feedback loops and downstream actions of ER target genes on growth factor pathways, compensatory signaling networks, influences of the tumor microenvironment and many others. Few of these mechanisms have been clinically validated.

Mechanisms of intrinsic resistance for the ETs tamoxifen and AIs have also been intensely debated for decades. Tamoxifen, has been the main treatment for premenopausal and postmenopausal women with ER+ metastatic breast cancer and as a chemo-preventative agent for women with a high risk of developing breast cancer. To exert its anti-cancer properties, tamoxifen must first be converted to its active form, endoxifen, by the polymorphic enzyme cytochrome P450 2D6 (CYP2D6). CYP2D6 is predominantly expressed in the liver and is involved in the metabolism of many commonly prescribed drugs, including antidepressants, anti-arrhythmics, anti-psychotics, β-blockers and tamoxifen. CYP2D6 is located on chromosome 22q13.1, and polymorphisms in this gene significantly affect activity. Between 6-10% of individuals are deficient in CYP2D6 metabolism and more than 75 CYP2D6 variants have been observed. Genetic analysis of CYP2D6 and tamoxifen efficacy remain unclear, some studies suggest that breast cancer patients with altered CYP2D6 have significantly poorer outcomes, while other studies show zero correlation. It is important to note that CYP2D6 activity can be reduced by co-administration of drugs such as selective serotonin reuptake inhibitors (SSRIs) and selective noradrenaline reuptake inhibitors (SNRIs) that are commonly co-prescribed with tamoxifen to alleviate undesirable side effects. Thus, independent of CYP2D6 genotype, additional factors such as diet, the microbiome, and co-drug administration may influence tamoxifen potency and in turn efficacy.

AIs are the other dominant class of ET. Their molecular target, aromatase, is encoded by CYP19A1 gene. Several polymorphisms of CYP19A1 have been identified that affect aromatase activity and AI binding in vitro. However these mutations do not correlate with AI efficacy in the clinic. Interestingly some mutations do correlate with increased or decreased risk of AI-associated muscoskeletal adverse events. AI side effects range from mild cases of arthralgia, myalgias and hot flashes to more severe side effects including increased risk of bone fracture. Both the efficacy and side effect profile of AIs are further confounded by their off-target effects. AIs have been demonstrated to bind to other CYP enzymes, such as letrozole which inhibits CYP2A6 and CYP2C19. The significance of this to determine AI response remains unknown. Thus, there is a critical need to uncover BoRs that go beyond genomics to determine which breast cancer patients will benefit from ET.

Here we report from a baseline plasma sample of 19 early stage breast cancer patients treated with ET, tamoxifen or aromatase inhibitors, we were able to identify metabolite biomarkers that perfectly differentiated patients that remained breast cancer-free with ET treatment compared to those who despite ET-treatment would relapse within 4-years. The level of these metabolite biomarkers function as a readout to predict and monitor ET response. Based on this signature initial ET may be adjusted, perhaps leading to co-treatment options. Further during treatment physicians can monitor the levels of these metabolites to determine if/when it necessary to change therapies. The results have tremendous clinical utility and could lead to a paradigm shift in how ET is used to treat and manage breast cancer.

Sample Characteristics:

Pretreatment plasma was collected from 19 ER+/HER− early stage breast cancer patients who were treated with ET tamoxifen or aromatase inhibitors.

Metabolite Extraction:

Plasma aliquots were thawed on ice and cleared via precipitation with ice-cold methanol (1:2 ratios v/v), vortexed, incubated −20° C. overnight, and centrifuged at 13,400 rcf for 30 min at 4° C. to pellet proteins. The supernatant was collected and dried overnight in a speed vac.

NMR Preparation & Analysis:

Dried metabolic extracts were resuspended in 200 μL of phosphate buffer (pH 7.4) in $D_2O$ containing 1 mM DSS and transferred to 3 mm NMR tubes. All samples were stored at 4° C. until analysis. 1D-$^1$H NMR and 2D $^1$H-$^{13}$C heteronuclear single quantum coherence spectroscopy (HSQC) spectra were collected on a Bruker 600 MHz spectrometer equipped with a cryoprobe. NMR data were processed using NMRPipe and proprietary Olaris software.

Statistics and Machine Learning:

A Wilcoxon non-parametric one-way analysis of variance was used to test for significant differences in measured metabolite resonances. Significantly altered or differentially expressed resonances were identified based on p-value<0.05. Subsequent analysis was limited to significantly altered variables. Non-supervised clustering techniques were used to visualize similarities between samples. To further discriminate samples we implored predictive modeling and machine learning algorithms.

Patient Characteristics

Baseline plasma was collected from 19 early stage breast cancer patients. These patients were defined as low-risk and were prescribed ET (tamoxifen or aromatase inhibitors) to manage their disease. Fourteen patients' tumors were controlled by ET, deemed ET responders ("R"). Five patients treated with ET developed metastasis within 4-years. These patients were characterized as ET non-responders ("NR"). Metastasis occurred in the brain, bones and lung with average onset within 1.9 years.

ET R Vs NR Display Significantly Different Baseline Metabolite Resonances

Figure 10A:
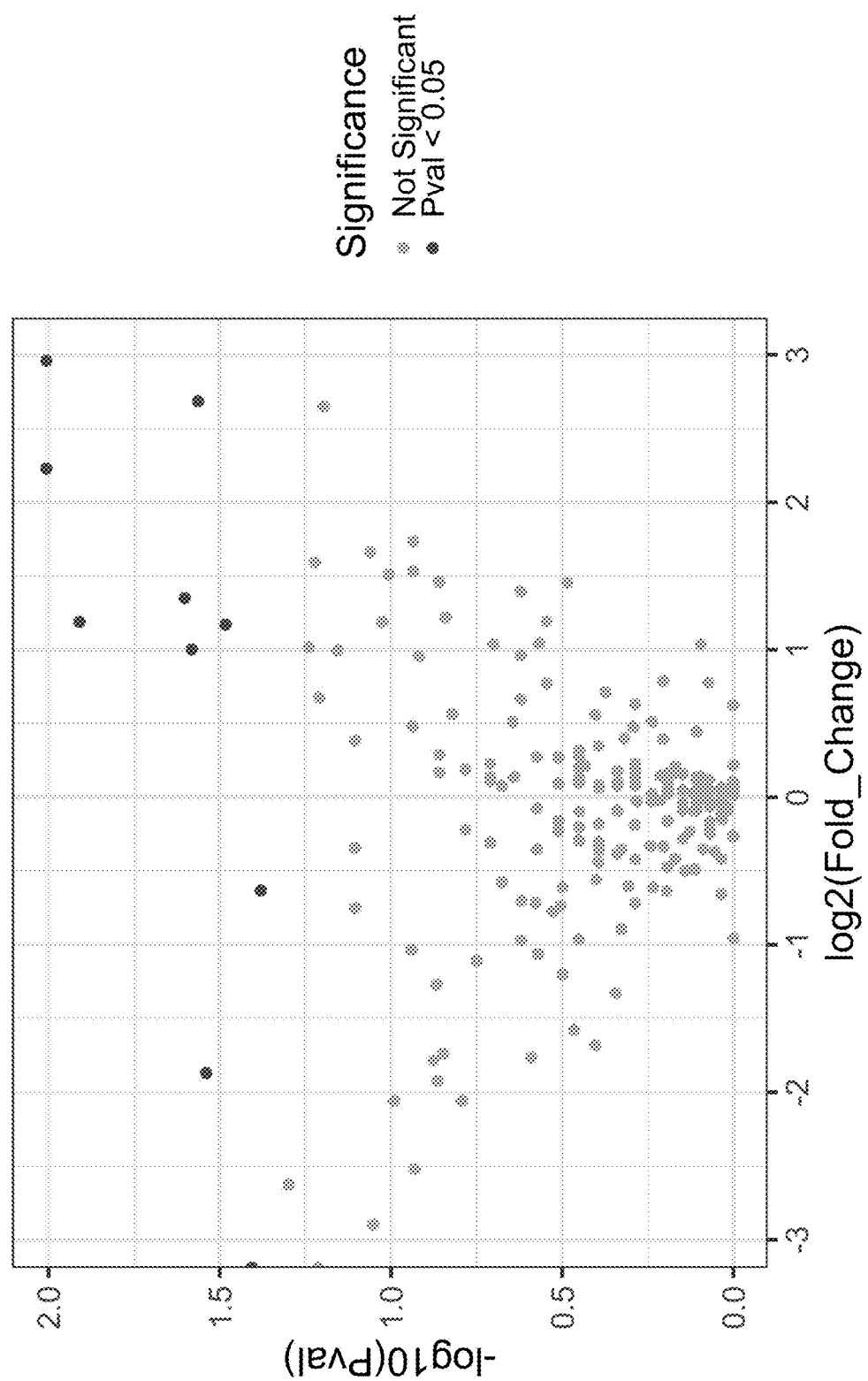
FIG. 10B. Shows violin plots of the top NMR grids that had largest difference in signal between ET R and NR patients from a baseline plasma sample.
Figure 10B:
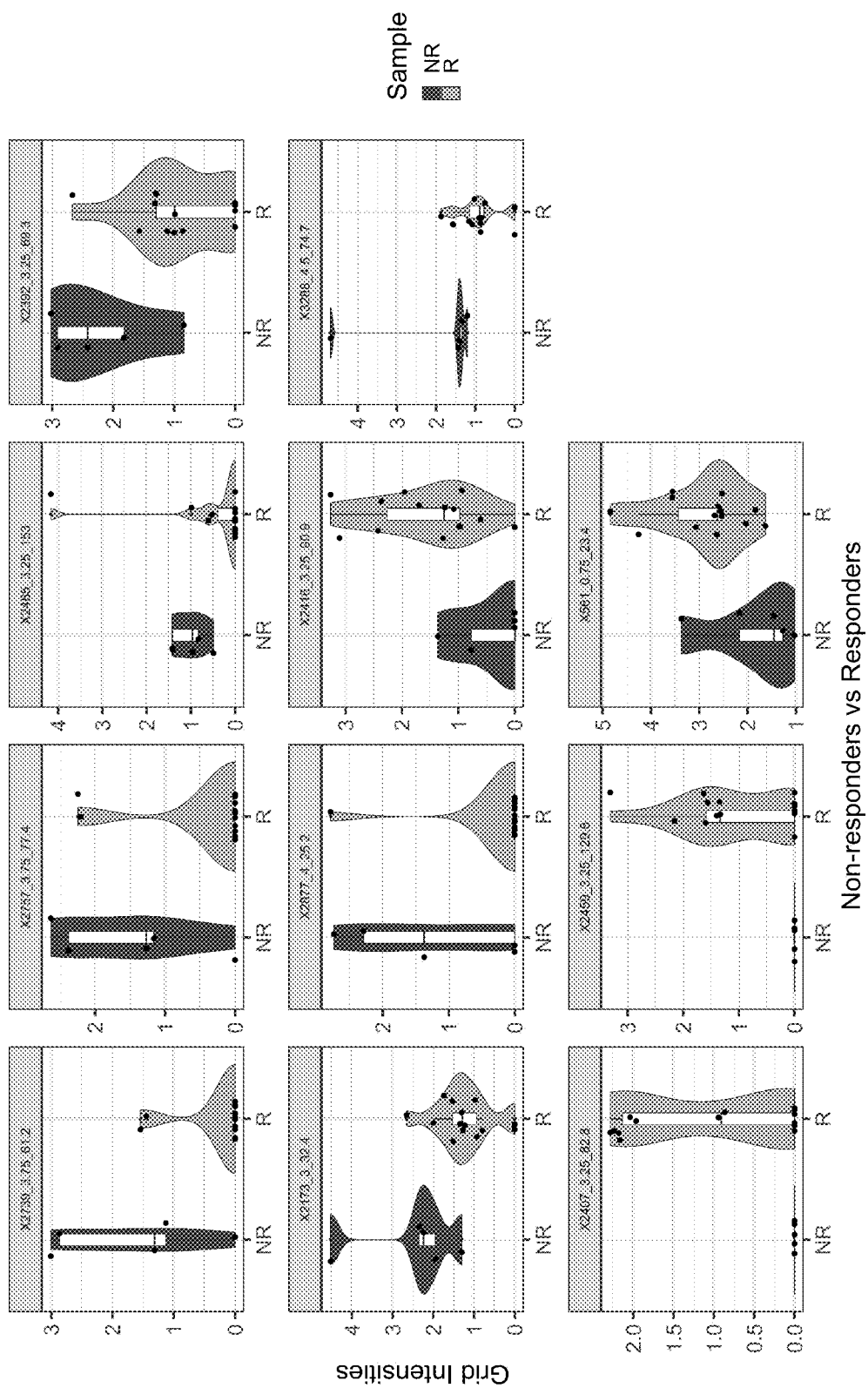

To gain a better understanding of the metabolite differences between R vs NR, we applied a "grid system" with a grid size of 0.25 ppm by 0.9 ppm in the $^1$H and $^{13}$C direction respectively across all spectra. Using the Wilcoxon test for significance, 11 grids differed between R and NR with a p-value of less than 0.05, shown in FIG. 10A. Violin plots for the entire 11 statistically different grids are shown in FIG. 10B. This is very close to the number of grids expected to differ by chance (10) for this dataset, suggesting rigorous scrutiny is needed to ensure biological significance.

Many metabolite resonances are higher in the R patients and lower in the NR patients or vice versa. For example, Grid #2739 (centered at 3.75 ppm in $^1$H and 61.2 ppm in $^{13}$C) and Grid #2416 (centered at 3.25 ppm in $^1$H and 90.9 ppm in $^{13}$C), provide examples of metabolite resonances significantly enriched in NR or R patients respectively (FIG. 10B).

BoR to Detect Trastuzumab Intrinsic Resistance

To uncover putative diagnostic features to discriminate R vs. NR we implored a series of statistical methods including principle component analysis (PCA), orthogonal partial least squares discriminate analysis (OPLS-DA), random forest (RF), naïve bayes, support vector machines (SVM) with radial kernel, SVM with linear kernel, generalized linear model, and CART. Due to the limited number of features that passed our test of significance, we further scrutinized the data to find the smallest set of metabolites, if any, that could differentiate R vs NR. We identified five features that were able to perfectly differentiate the ET R and NR patients. The metabolites and/or metabolite resonances that differentiate ET R and NR patients are listed in FIG. 11. The relative expression of these metabolites and/or metabolite resonances could be used to screen future ER+ patients to predict duration of response to ET.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating a patient, comprising:
   obtaining a sample from a patient wherein the sample is selected from the group consisting of blood, urine, feces, cerebral fluid, saliva and tissue extract;
   analyzing a component of the sample using NMR spectroscopy;
   obtaining an array of data on the sample from the NMR spectroscopy;
   comparing the array of data to data of a statistically significant number of patients administered a CDK4/6 drug;
   determining a Biomarker of Response in patients based on patient response to the CDK4/6 drug;
   counseling the patient regarding medical options based on determining the Biomarker of Response;
   administering the CDK4/6 drug to the patient wherein the patient has been predetermined as a responder to the CDK4/6 drug based on having the Biomarker of Response.

2. The method of claim 1, wherein the spectroscopy is carried out by using 2D $^1$H-$^{13}$C HSQC NMR spectroscopy.

3. The method of claim 1, wherein the CDK4/6 drug has been approved for use only when the patient has been predetermined as a responder to the drug based on the Biomarker of Response.

4. A method of selecting a population of patients, comprising:
   (a) administering to a group of patients a CDK4/6 drug over a period of time;
   (b) analyzing a metabolite in a biological sample obtained from the patients, wherein the sample is selected from the group consisting of blood, urine, feces, cerebral fluid, saliva and tissue extract of the group of patients at a first point in time;
   (c) analyzing the metabolite in the sample of the group of patients at a second point in time different from the first point in time;
   (d) comparing results of the analyzing in (b) with the analyzing in (c) to obtain a differential; and
   (e) relating the differential to how a patient responds to the CDK4/6 drug thereby determining responders to the CDK4/6 drug, which are selected for treatment with the CDK4/6 drug.

5. The method as claimed in claim 4, further comprising:
   (f) counseling a patient on how the differential obtained in (d) relates to a patient's likely response to a CDK4/6 drug.

6. A method of selecting a population of patients, comprising:
   (a) analyzing a metabolite in a biological sample selected from the group consisting of blood, urine, feces, cerebral fluid, saliva and tissue extract of a group of patients taking a CDK4/6 drug at a first point in time;
   (b) continuing to administer to the group of patients the CDK4/6 drug over a period of time;

(c) analyzing the metabolite in the sample of the group of patients at a second point in time different from the first point in time;

(d) comparing results of the analyzing in (a) with the analyzing in (c) to obtain a differential;

(e) relating the differential to how a patient responds to the CDK4/6 drug thereby determining responders to the CDK4/6 drug, which are selected for further treatment with the drug CDK4/6.

7. The method of claim 6, further comprising:

(f) counseling a patient regarding likelihood of responding to the CDK4/6 drug.

8. The method of claim 5, wherein the analyzing is by spectrographic analysis using NMR.

9. The method of determining a point at which a patient develops resistance to a CDK4/6 drug, comprising:

(a) analyzing a metabolite in a human biological sample of a patient at a first point in time wherein the patient is being treated with a CDK4/6 drug;

(b) continuing to treat the patient over time with the CDK4/6 drug;

(c) analyzing the sample of the patient at a point in time different from the analyzing in step (a);

(d) comparing the analyzing of (a) with the analyzing of (c) to obtain a differential; and (e) relating the differential to a standard in order to determine if the patient has developed a resistance to the CDK4/6 drug.

10. The method of claim 9, further comprising:

counseling the patient regarding developing resistance to the CDK4/6 drug; and discontinuing administration of the CDK4/6 drug to the patient when it is determined by comparison of the differential to a standard that the patient has developed resistance to the CDK4/6 drug.

11. The method of claim 9, wherein the analyzing steps (a) and (c) are begun within 4 hours or less after extraction of the sample from the patient.

12. The method of claim 9, wherein the analyzing step is begun within 15 minutes or less after extraction of the sample from the patient.

13. The method of claim 9, further comprising:

Preserving the sample after extraction from a patient and before the analyzing step (a) or (c).

14. The method of claim 13, wherein the preserving step comprises contacting the sample with a preservative.

15. The method of claim 13, wherein the sample is blood and the preserving step comprises putting blood into a tube that contains a preservative.

16. The method of claim 15, wherein the preserving step comprises reducing the temperature of the sample.

17. The method of claim 14, wherein the preserving step comprises freezing the sample.

18. A method of treating a patient, comprising:

(a) analyzing a sample obtained from a patient being treated with a CDK4/6 drug using spectroscopy;

(b) obtaining data from the spectroscopy;

(c) comparing the data obtained in (b) with data obtained from a statistically significant sample of patients treated with the same CDK4/6 drug in order to determine a differential;

(d) continuing to treat the patient with the CDK4/6 drug overtime while periodically repeating steps (a), (b), and (c); and (e) counseling the patient with respect to the significance of the differential obtained; and (f) modifying treatment of the patient based on the differential.

19. The method as claimed in claim 18, wherein the patient is a cancer patient, the CDK4/6 drug is a cancer drug and the spectroscopy is nuclear magnetic residence (NMR) spectroscopy.

* * * * *